(12) United States Patent
Ota et al.

(10) Patent No.: US 9,937,084 B2
(45) Date of Patent: Apr. 10, 2018

(54) ABSORBENT BODY AND ABSORBENT ARTICLE USING THE SAME

(71) Applicant: LIVEDO CORPORATION, Shikokuchuo-shi, Ehime (JP)

(72) Inventors: Yoshihisa Ota, Mima-gun (JP); Motoko Nishida, Mima-gun (JP)

(73) Assignee: LIVEDO CORPORATION, Shikokuchuo-shi (JP)

( * ) Notice: Subject to any disclaimer, the term of this patent is extended or adjusted under 35 U.S.C. 154(b) by 68 days.

(21) Appl. No.: 14/422,320

(22) PCT Filed: Aug. 30, 2013

(86) PCT No.: PCT/JP2013/005135
§ 371 (c)(1),
(2) Date: Feb. 18, 2015

(87) PCT Pub. No.: WO2014/034134
PCT Pub. Date: Mar. 6, 2014

(65) Prior Publication Data
US 2015/0224000 A1    Aug. 13, 2015

(30) Foreign Application Priority Data
Aug. 31, 2012   (JP) .................................. 2012-192186

(51) Int. Cl.
*A61F 13/495*   (2006.01)
*A61F 13/537*   (2006.01)
(Continued)

(52) U.S. Cl.
CPC .......... *A61F 13/5323* (2013.01); *A61F 13/15* (2013.01); *A61F 13/495* (2013.01); *A61F 13/535* (2013.01); *A61F 13/53756* (2013.01)

(58) Field of Classification Search
CPC .................. A61F 13/53756; A61F 2013/4956
See application file for complete search history.

(56) References Cited

U.S. PATENT DOCUMENTS 2,820,716 A * 1/1958 Plummer ................. D04H 1/62
118/636
2,880,113 A * 3/1959 Drelich .................... D04H 1/62
162/184
(Continued)

FOREIGN PATENT DOCUMENTS

EP    1 614 408 A1   1/2006
JP    02-60645 A     3/1990
(Continued)

OTHER PUBLICATIONS

Particle definition, The American Heritage(R) Dictionary of the English Language, 2011.*
(Continued)

*Primary Examiner* — Paula L Craig
(74) *Attorney, Agent, or Firm* — Westerman, Hattori, Daniels & Adrian

(57) ABSTRACT

[Object]
To provide an absorbent article and an absorbent body having excellent absorption performance.
[Solution]
The present invention provides an absorbent body having at least two or more layers, the absorbent body comprising: a water absorption layer having a water absorption region where a water absorbent resin powder is disposed and a thickness-direction-penetrating opening region; and a layer having a diffusion region where a diffusibility improvement material having an under-load liquid passing rate of 15 seconds or less is disposed, as a lower layer of the water absorption layer, wherein the lower layer has the diffusion region disposed at least a part of a portion located below the opening region.

10 Claims, 7 Drawing Sheets

(51) Int. Cl.
*A61F 13/532* (2006.01)
*A61F 13/535* (2006.01)
*A61F 13/15* (2006.01)

(56) References Cited

U.S. PATENT DOCUMENTS

| | | | | |
|---|---|---|---|---|
| 4,381,783 | A * | 5/1983 | Elias | A61L 15/18 604/368 |
| 4,988,344 | A * | 1/1991 | Reising | A61F 13/535 604/358 |
| 4,988,345 | A | 1/1991 | Reising | |
| 5,300,054 | A * | 4/1994 | Feist | A61F 13/15203 604/358 |
| 5,304,161 | A * | 4/1994 | Noel | A61F 13/15203 604/358 |
| 5,306,266 | A * | 4/1994 | Freeland | A61F 13/495 604/358 |
| 5,324,561 | A * | 6/1994 | Rezai | A61F 13/537 428/220 |
| 5,342,337 | A * | 8/1994 | Runeman | A61F 13/535 604/378 |
| 5,614,283 | A | 3/1997 | Potnis et al. | |
| 5,643,238 | A * | 7/1997 | Baker | A61F 13/5323 156/276 |
| 5,669,894 | A * | 9/1997 | Goldman | A61L 15/42 604/366 |
| 5,986,167 | A * | 11/1999 | Arteman | A61F 13/533 604/380 |
| 6,118,042 | A | 9/2000 | Palumbo | |
| 6,291,050 | B1 | 9/2001 | Cree et al. | |
| 6,372,952 | B1 | 4/2002 | Lash et al. | |
| 6,420,626 | B1 * | 7/2002 | Erspamer | A61F 13/15617 428/131 |
| 6,423,884 | B1 * | 7/2002 | Oehmen | A61F 13/495 604/369 |
| 6,726,668 | B2 * | 4/2004 | Underhill | A61F 13/42 604/378 |
| 6,727,403 | B1 * | 4/2004 | Ehrnsperger | A61F 13/15203 604/358 |
| 7,122,023 | B1 * | 10/2006 | Hinoki | A61F 13/47227 604/378 |
| 2001/0021833 | A1 * | 9/2001 | Schmidt | A61F 13/475 604/385.01 |
| 2002/0187302 | A1 * | 12/2002 | Koslow | A61F 13/15658 428/114 |
| 2003/0023213 | A1 * | 1/2003 | Fernfors | A61F 13/47218 604/359 |
| 2003/0078349 | A1 * | 4/2003 | Tagawa | A61F 13/15203 526/89 |
| 2003/0097113 | A1 * | 5/2003 | Molee | A61F 13/53747 604/385.101 |
| 2003/0135177 | A1 * | 7/2003 | Baker | A61F 13/15634 604/368 |
| 2003/0195487 | A1 | 10/2003 | Thomas | |
| 2004/0019342 | A1 * | 1/2004 | Nagasuna | A61F 13/15203 604/385.01 |
| 2004/0024104 | A1 * | 2/2004 | Ota | A61F 13/53 524/492 |
| 2004/0086480 | A1 * | 5/2004 | Worley | A01N 59/00 424/78.22 |
| 2004/0087927 | A1 * | 5/2004 | Suzuki | A61F 13/512 604/378 |
| 2004/0162536 | A1 * | 8/2004 | Becker | A61F 13/15203 604/367 |
| 2004/0193129 | A1 * | 9/2004 | Guidotti | A61F 13/535 604/378 |
| 2004/0243078 | A1 * | 12/2004 | Guidotti | A61F 13/15203 604/367 |
| 2006/0116651 | A1 | 6/2006 | Kurita et al. | |
| 2007/0135787 | A1 * | 6/2007 | Raidel | A61F 13/15707 604/383 |
| 2007/0197987 | A1 * | 8/2007 | Tsang | A61F 13/15658 604/365 |
| 2007/0225663 | A1 * | 9/2007 | Watt | A61M 1/0088 604/313 |
| 2008/0269707 | A1 * | 10/2008 | Song | A61F 13/42 604/385.01 |
| 2009/0270825 | A1 * | 10/2009 | Wciorka | A61F 13/495 604/367 |
| 2010/0228215 | A1 * | 9/2010 | Ponomarenko | A61F 13/495 604/374 |
| 2011/0060303 | A1 * | 3/2011 | Bissah | A61F 13/4756 604/372 |
| 2014/0364824 | A1 * | 12/2014 | Ota | A61L 15/42 604/372 |
| 2014/0378926 | A1 * | 12/2014 | Ota | A61F 13/5323 604/367 |
| 2015/0065980 | A1 * | 3/2015 | Ota | A61F 13/537 604/372 |
| 2015/0209197 | A1 * | 7/2015 | Ota | A61F 13/53 604/372 |
| 2015/0297424 | A1 * | 10/2015 | Ota | A61L 15/60 604/372 |

FOREIGN PATENT DOCUMENTS

| | | |
|---|---|---|
| JP | H08-229071 A | 9/1996 |
| JP | 2002-528302 A | 9/2002 |
| JP | 2004-1355 A | 1/2004 |
| JP | 2006-057075 A | 3/2006 |
| JP | 2006-524112 A | 10/2006 |
| JP | 2008-237430 A | 10/2008 |
| JP | 2011-19896 A | 2/2011 |
| JP | 2011-55959 A | 3/2011 |
| JP | 2012-024206 A | 2/2012 |
| WO | 95/24878 A1 | 9/1995 |
| WO | 96/19173 A1 | 6/1996 |
| WO | 97/34559 A1 | 9/1997 |

OTHER PUBLICATIONS

International Search Report dated Jan. 22, 2014 issued in corresponding application No. PCT/JP2013/005135.

Written Opinion of the International Searching Authority dated Jan. 22, 2014 issued in corresponding application No. PCT/JP2013/005135.

Office Action dated Jun. 28, 2016, issued in counterpart to Japanese Patent Application No. 2012-192186. (2 pages).

Office Action dated Jan. 17, 2017, issued in counterpart Japanese Patent Application No. 2012-192186, with English translation. (6 pages).

* cited by examiner

[Fig. 1]
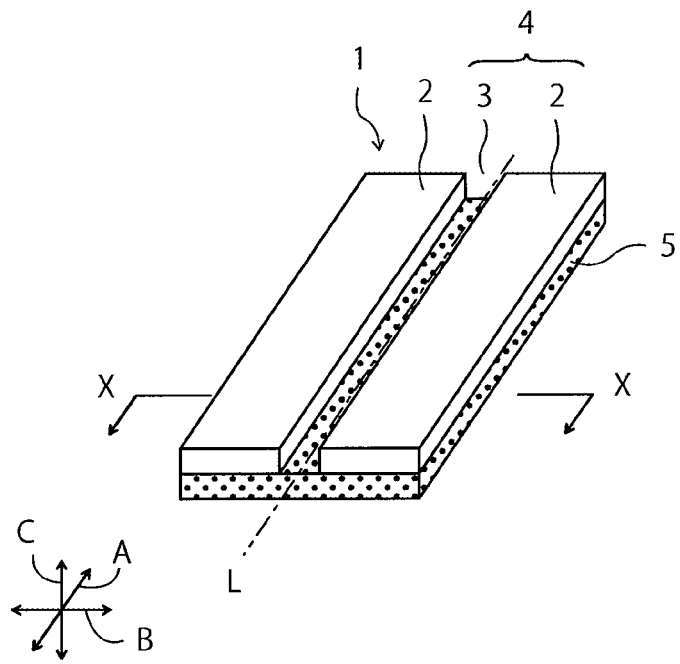
[Fig. 2]
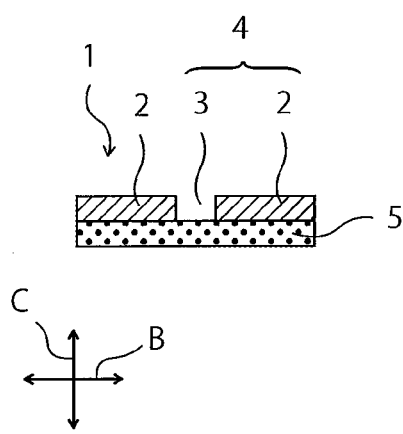

[Fig. 3]
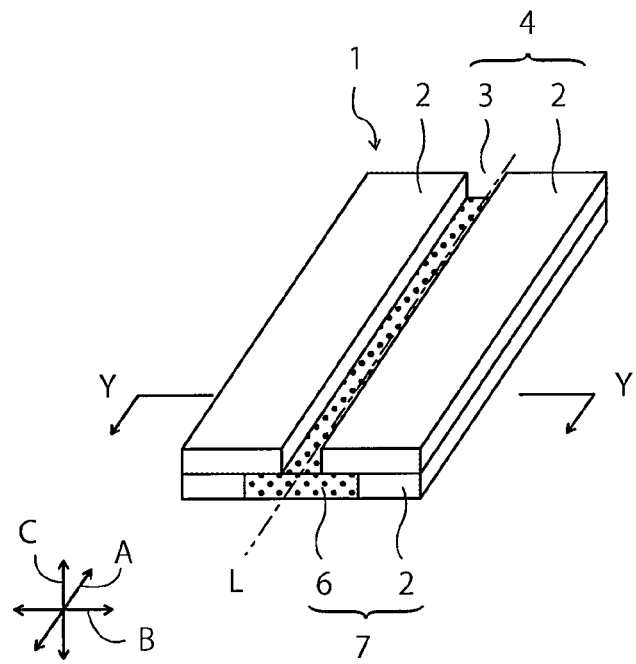
[Fig. 4]
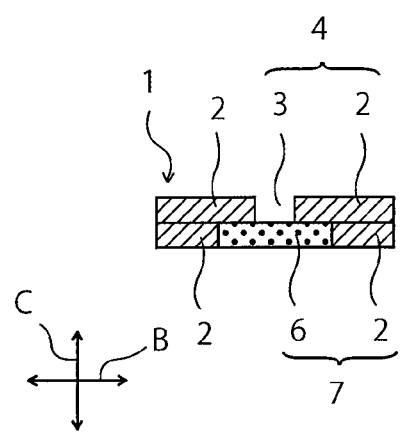

[Fig. 5]
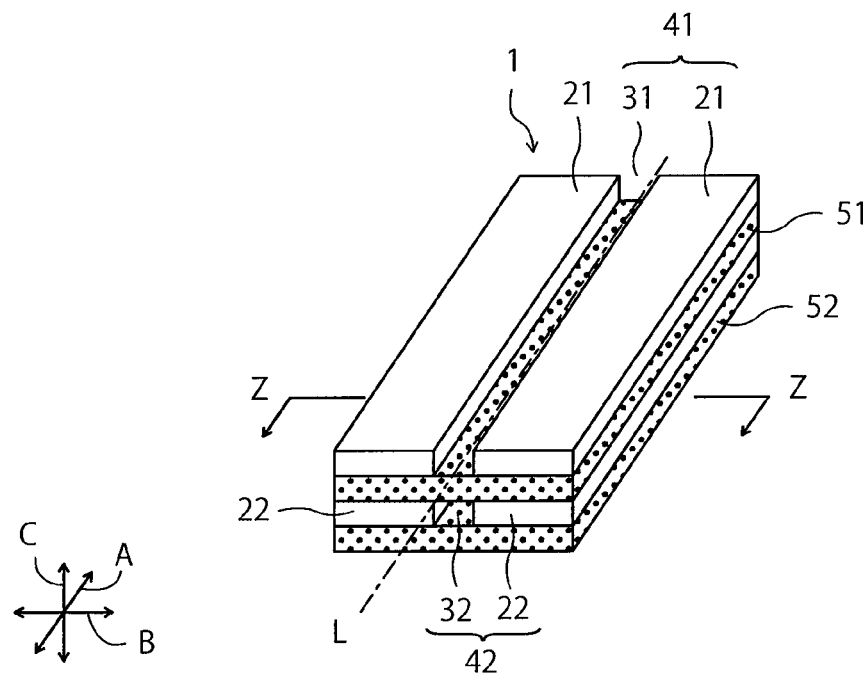
[Fig. 6]
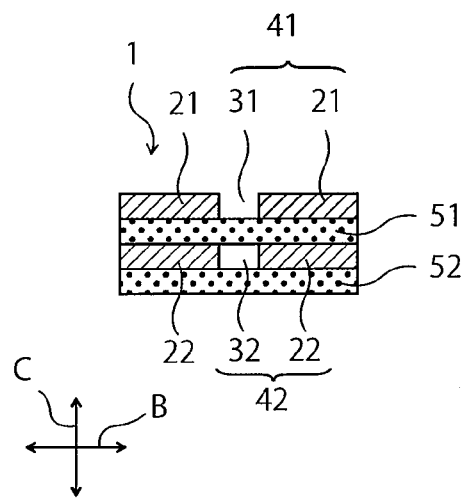

[Fig. 7]
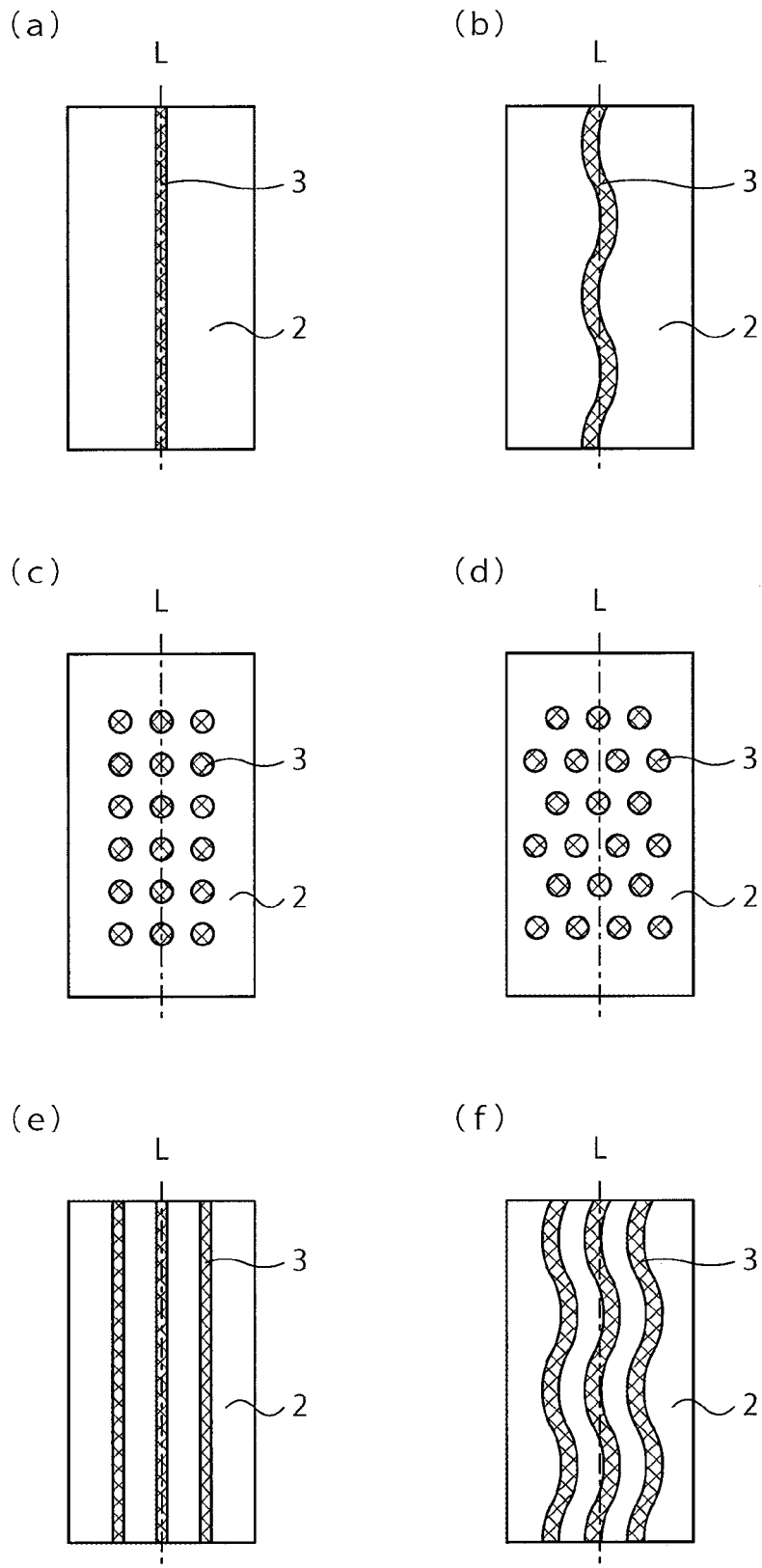

[Fig. 8]
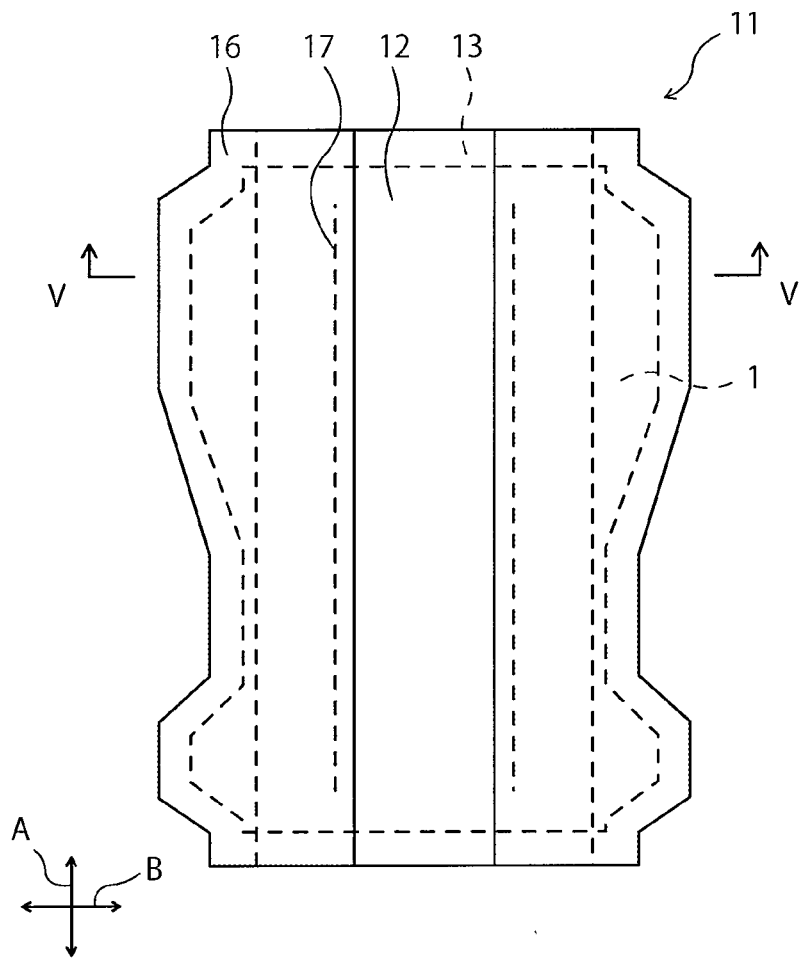
[Fig. 9]
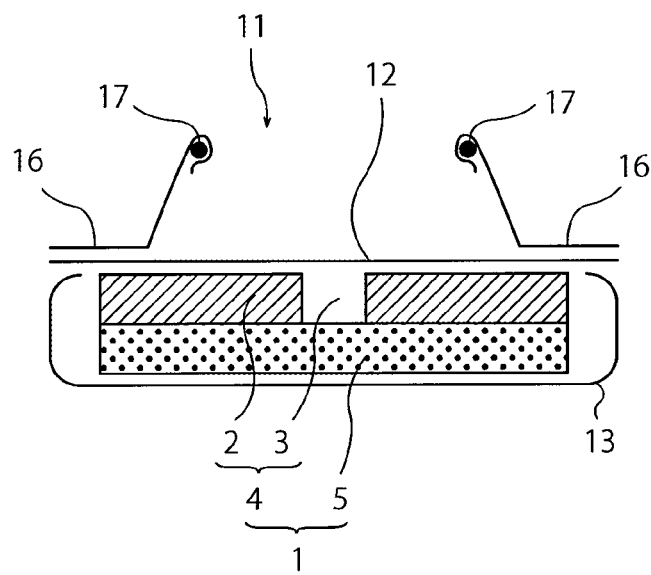

[Fig. 10]
(a)
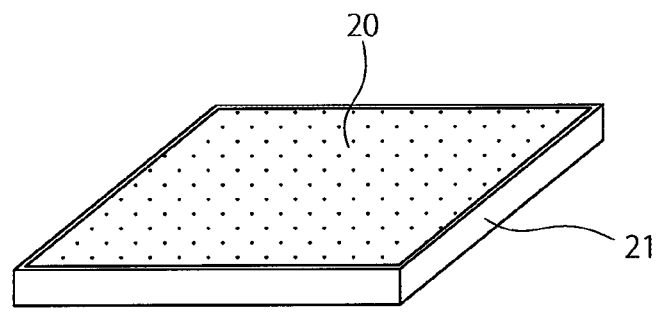
(b)
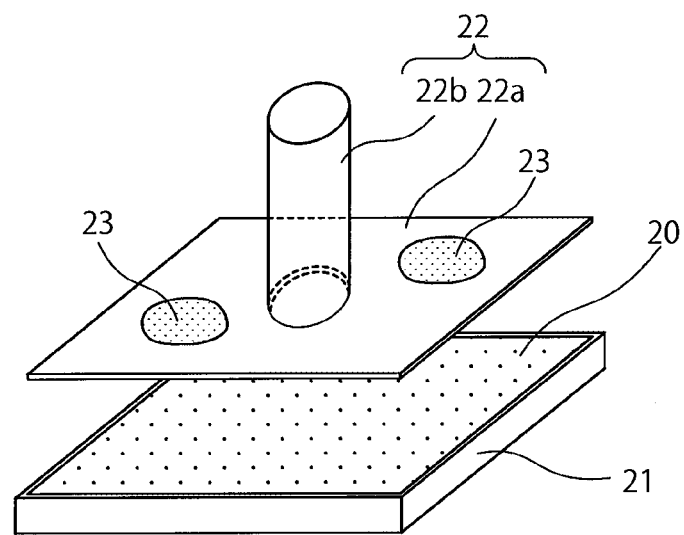

[Fig. 11]
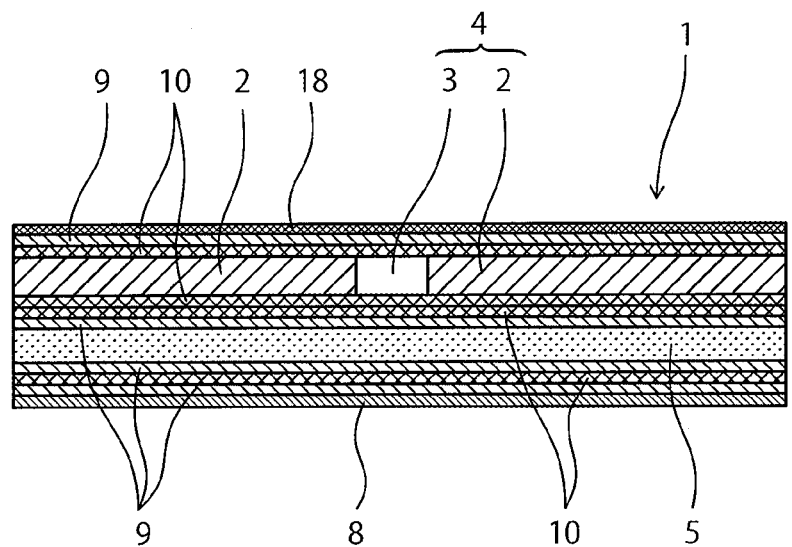
[Fig. 12]
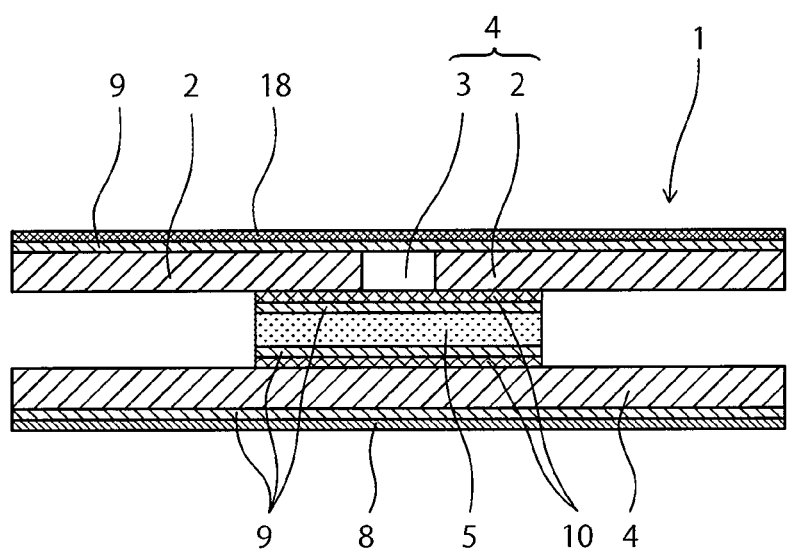

ABSORBENT BODY AND ABSORBENT ARTICLE USING THE SAME

TECHNICAL FIELD

The present invention relates to an absorbent body used in absorbent articles such as incontinence pads, disposable diapers, and sanitary napkins; and the present invention particularly relates to an improvement technology regarding absorption performance of an absorbent body.

BACKGROUND ART

Absorbent articles such as incontinence pads, disposable diapers, and sanitary napkins include an absorbent body for absorbing and retaining body fluid excreted from body such as urine and menstrual blood. The absorbent body generally includes a water absorbent resin powder, and body fluid or the like is absorbed and retained in the water absorbent resin powder inside the absorbent body. There have been proposals of water absorbent articles having an absorbent body with improved absorption rate of body fluid or the like.

For example, Patent Literature 1 proposes an absorbent article comprising a liquid permeable top sheet, a liquid impermeable back sheet, and an absorbent core interposed therebetween, wherein a second sheet formed from a nonwoven fabric having a hollow fiber is interposed between the top sheet and the absorbent core.

Patent Literature 2 proposes an absorption product comprising: (a) a top sheet comprising an aperture polymeric film web having a first surface, and a second surface generally parallel to and spaced from the first surface, and a plurality of fluid passageways extending between the first surface and the second surface in fluid communication with one another, the web being formed of a polymeric film comprising at least one bulk modified layer, the bulk modified layer comprising a substantially homogeneous stabilized dispersion of a hydrophobic additive in a polymer material; (b) a back sheet peripherally joined with the top sheet; and (c) an absorbent core positioned between the second surface of the top sheet and the back sheet.

Patent Literature 3 proposes an absorbent article comprising: a top sheet; a back sheet; and an intermediate layer between the top sheet and the back sheet; wherein at least one of the top sheet, back sheet, and intermediate layer comprises a three-dimensional vacuum formed film with a male side void volume of at least 350 cc/m$^2$; and the absorbent article having a first minute decrease in temperature of at least 8 degrees F. in a Third Insult Test.

CITATION LIST

Patent Literature

[PTL 1]
Japanese Patent Publication No. 2011-055959
[PTL 2]
Japanese Patent Publication No. 2002-528302
[PTL 3]
Japanese Patent Publication No. 2006-524112

SUMMARY OF INVENTION

Technical Problem

The under-load liquid passing properties have been found to be inferior in all of the nonwoven fabric, the polymeric film web and the three-dimensional vacuum formed film with a void volume (cf. Patent Literature 1 to 3), which have been used conventionally for improving a water absorbent article's absorption rate of body fluid or the like. Thus, the absorption rate of body fluid or the like has been insufficient when a load is applied on the water absorbent article. Furthermore, in particular, films having holes such as those used in Patent Literature 2 and 3 have a problem that liquid may easily remain in the voids within the film and cause rashes.

The present invention has been made in view of the above described circumstances; and an objective of the present invention is to provide an absorbent body having an excellent absorption rate of body fluid or the like and excellent dryness after absorbing the body fluid or the like, and an absorbent article using the absorbent body.

Solution to Problem

The present invention is directed to an absorbent body having at least two or more layers, the absorbent body comprising:

a water absorption layer having a water absorption region where a water absorbent resin powder is disposed and a thickness-direction-penetrating opening region; and a layer having a diffusion region where a diffusibility improvement material having an under-load liquid passing rate of 15 seconds or less is disposed, as a lower layer of the water absorption layer, wherein the lower layer has the diffusion region disposed at least a part of a portion located below the opening region.

Since the water absorption layer has the opening region and the diffusion region is formed at least partially below the opening region, a portion of body fluid or the like passes through the opening region and is taken into the diffusion region. The body fluid or the like taken into the diffusion region is diffused within the diffusion region in a planar direction, and is absorbed from a bottom surface (external surface) side of the water absorption layer. Thus, since the body fluid or the like is absorbed from both the top surface and the bottom surface of the water absorption layer, the absorption area increases. As a result, the absorbent body of the present invention has a fast absorption rate. In addition, the body fluid or the like absorbed from the bottom surface side of the water absorption layer does not pass through the water absorption layer and return to the top surface (skin surface) side. Therefore, the absorbent body of the present invention has excellent dryness after absorbing the body fluid or the like.

A suitable planar view shape of the diffusion region of the lower layer is a circular shape, an elliptical shape, a polygonal shape, a polygonal shape having rounded corners, or a slit shape. In addition, the lower layer is preferably a diffusion layer only having the diffusion region. Preferably, the opening region is formed in a slit shape. The water absorption layer preferably includes a water absorbent resin powder satisfying the following requirements:

Absorption ratio: 50 g/g or more; and
Water retention amount: 25 g/g or more.

The present invention also includes an absorbent article having the above absorbent body.

Advantageous Effects of the Invention

The absorbent body and the absorbent article of the present invention have excellent absorption rate of body fluid or the like, and excellent dryness after absorbing the body fluid or the like.

BRIEF DESCRIPTION OF DRAWINGS

FIG. 1 is a schematic perspective view of an absorbent body according to a preferable Embodiment 1 of the present invention.

FIG. 2 is a cross sectional view along line X-X in FIG. 1.

FIG. 3 is a schematic perspective view of an absorbent body according to a preferable Embodiment 2 of the present invention.

FIG. 4 is a cross sectional view along line Y-Y in FIG. 3.

FIG. 5 is a schematic perspective view of an absorbent body according to a preferable Embodiment 3 of the present invention.

FIG. 6 is a cross sectional view along line Z-Z in FIG. 5.

FIG. 7 is a plan view showing how an opening region is formed in a water absorption layer.

FIG. 8 is a schematic plan view of an absorbent article according to a preferable embodiment of the present invention.

FIG. 9 is a cross sectional view along line V-V in FIG. 8.

FIG. 10 is a schematic diagram for describing a method for measuring an under-load liquid passing rate of a diffusibility improvement material.

FIG. 11 is a schematic sectional view of an absorbent body No. 1 in an example.

FIG. 12 is a schematic sectional view of an absorbent body No. 2 in an example.

DESCRIPTION OF EMBODIMENTS

The present invention provides an absorbent body having at least two or more layers, the absorbent body comprising:

a water absorption layer having a water absorption region where a water absorbent resin powder is disposed and a thickness-direction-penetrating opening region; and a layer having a diffusion region where a diffusibility improvement material having an under-load liquid passing rate of 15 seconds or less is disposed, as a lower layer of the water absorption layer, wherein the lower layer has the diffusion region disposed at least a part of a portion located below the opening region.

Since the water absorption layer has the opening region and the diffusion region is formed at least partially below the opening region, a portion of body fluid or the like passes through the opening region and is taken into the diffusion region. The body fluid or the like taken into the diffusion region is diffused within the diffusion region in a planar direction, and is absorbed from a bottom surface (external surface) side of the water absorption layer. In other words, since the body fluid or the like is absorbed from both the top surface and the bottom surface of the water absorption layer, the absorption area increases. As a result, the absorbent body of the present invention has a fast absorption rate. In addition, the body fluid or the like absorbed from the bottom surface side of the water absorption layer does not pass through the water absorption layer and return to the top surface (skin surface) side. Therefore, the absorbent body of the present invention has absolutely excellent dryness after absorbing body fluid or the like. Thus, the absorbent body of the present invention is suitable for an absorbent article for sensitive skin, since the absorbent body of the present invention can improve dryness on the skin surface side of a user of a water absorption layer.

Water Absorbent Resin Powder

First, description will be provided for a water absorbent resin powder used in the present invention. The water absorbent resin powder is at least included in the water absorption layer, and may be contained in the layer having the diffusion region. The water absorbent resin powder used in the present invention is preferably a crosslinked polymer (A) mainly composed of acrylic acid having carboxy groups thereof being at least partially neutralized. The percentage content of the acrylic acid component forming the crosslinked polymer is preferably 90 mass % or more and more preferably 95 mass % or more, and is preferably 99 mass % or less and more preferably 97 mass % or less. If the percentage content of the acrylic acid component is within the above described range, the obtained water absorbent resin powder can easily express a desired absorption performance.

Examples of cations for neutralizing at least a part of the carboxyl groups of the crosslinked polymer (A) include, but not particularly limited to, alkali metal ions such as lithium, sodium, and potassium; and alkaline earth metal ions such as magnesium and calcium. Of those described above, at least a part of the carboxyl groups of the crosslinked polymer is preferably neutralized with the sodium ion. It should be noted that, with regard to neutralization of the carboxyl groups of the crosslinked polymer, neutralization may be conducted on the carboxyl groups of the crosslinked polymer which has been obtained by polymerization or neutralization may be conducted in advance on a monomer which is then used for forming the crosslinked polymer.

The degree of neutralization of the carboxyl groups of the crosslinked polymer is preferably 60 mole % or more, and more preferably 65 mole % or more. This is because there are cases where the absorption performance of the obtained water-absorbent resin powder deteriorates if the degree of neutralization is too low. Furthermore, there is no particular limitation on the upper limit of the degree of neutralization, and all the carboxyl groups may be neutralized. It should be noted that the degree of neutralization is obtained by the following formula.

Degree of neutralization (mole %)=100×[Number of moles of neutralized carboxyl groups in the crosslinked polymer]/[Total number of moles of the carboxyl groups in the crosslinked polymer (including neutralized and unneutralized groups)]

The crosslinked polymer (A) preferably includes those obtained by polymerization of the unsaturated monomer composition containing a water-soluble ethylenically unsaturated monomer (a1)) and/or a hydrolyzable monomer (a2) producing the water-soluble ethylenically unsaturated monomer (a1)) by hydrolysis and an internal crosslinking agent (b).

The water-soluble ethylenically unsaturated monomer (a1)) is not particularly limited, but a monomer having at least one water-soluble substituent and an ethylenically unsaturated group, or the like can be used. The water-soluble monomer means a monomer having a property of being dissolved in an amount of at least 100 g in 100 g of water at 25 degrees centigrade. In addition, the hydrolyzable monomer (a2) is hydrolyzed with water at 50 degrees centigrade, by the action of a catalyst (an acid, a base, or the like) where necessary, to produce the water-soluble ethylenically unsaturated monomer (a1). The hydrolysis of the hydrolyzable monomer (a2) may be conducted during or after the polymerization of the crosslinked polymer (A) or both during and after the polymerization of the crosslinked polymer (A). However, the hydrolysis of the hydrolyzable monomer (a2) is preferably conducted after the polymerization of the crosslinked polymer (A) in light of the molecular weight of the obtained water-absorbent resin powder and the like.

Examples of the water-soluble substituent include a carboxyl group, a sulfo group, a sulfoxy group, a phosphono group, a hydroxyl group, a carbamoyl group, an amino group, or salts thereof and an ammonium salt. A salt of a carboxyl group (a carboxylate), a salt of a sulfo group (a sulfonate), and an ammonium salt are preferred. In addition, examples of the salts include salts of alkali metal such as lithium, sodium, and potassium and salts of alkaline earth metal such as magnesium and calcium. The ammonium salt may be any of salts of primary to tertiary amines or a quaternary ammonium salt. Of these salts, in light of absorption properties, alkali metal salts and ammonium salts are preferred, and alkali metal salts are more preferred, and sodium salts are further preferred.

As the water-soluble ethylenically unsaturated monomer having a carboxyl group and/or a salt thereof, an unsaturated carboxylic acid having 3 to 30 carbon atoms and/or a salt thereof are preferred. Specific examples of the water-soluble ethylenically unsaturated monomer having a carboxyl group and/or a salt thereof include unsaturated monocarboxylic acids and/or salts thereof such as (meth)acrylic acid, (meth)acrylic acid salt, crotonic acid, and cinnamic acid; unsaturated dicarboxylic acids and/or salts thereof such as maleic acid, maleate, fumaric acid, citraconic acid, and itaconic acid; and monoalkyl (1 to 8 carbon atoms) esters of unsaturated dicarboxylic acids and/or salts thereof such as maleic acid monobutyl ester, fumaric acid monobutyl ester, ethylcarbitol monoester of maleic acid, ethylcarbitol monoester of fumaric acid, citraconic acid monobutyl ester, and itaconic acid glycol monoester. It is noted that in the description of the present invention, "(meth)acrylic" means "acrylic" and/or "methacrylic".

As a water-soluble ethylenically unsaturated monomer having a sulfo group and/or a salt thereof, a sulfonic acid having 2 to 30 carbon atoms and/or a slat thereof are preferred. Specific examples of the water-soluble ethylenically unsaturated monomer having a sulfo group and/or a salt thereof include aliphatic or aromatic vinyl sulfonic acids such as vinyl sulfonic acid, (meth)allyl sulfonic acid, styrene sulfonic acid, and alpha-methyl styrene sulfonic acid; (meth)acryloyl-containing alkyl sulfonic acids such as (meth)acryloxy propyl sulfonic acid, 2-hydroxy-3-(meth)acryloxy propyl sulfonic acid, 2-(meth)acryloylamino-2,2-dimethylethane sulfonic acid, 3-(meth)acryloxyethane sulfonic acid, 2-(meth)acrylamide-2-methylpropane sulfonic acid, and 3-(meth)acrylamide-2-hydroxypropane sulfonic acid; and alkyl(meth)allyl sulfosuccinate.

Examples of a water-soluble ethylenically unsaturated monomer having a sulfoxy group and/or a salt thereof include sulfate ester of hydroxyalkyl(meth)acrylate; and sulfate ester of polyoxyalkylene mono(meth)acrylate.

Examples of a water-soluble ethylenically unsaturated monomer having a phosphono group and/or a salt thereof include phosphate monoesters of (meth)acrylic acid hydroxyalkyl, phosphate diesters of (meth)acrylic acid hydroxyalkyl, and (meth)acrylic acid alkylphosphonic acids.

Examples of a water-soluble ethylenically unsaturated monomer having a hydroxyl group include mono-ethylenically unsaturated alcohols having 3 to 15 carbon atoms such as (meth)allyl alcohol and (meth)propenyl alcohol; mono-ethylenically unsaturated carboxylates or mono-ethylenically unsaturated ethers of bivalent to hexavalent polyols such as alkylene glycol having 2 to 20 carbon atoms, glycerin, sorbitan, diglycerin, pentaerythritol, and polyalkylene (2 to 4 carbon atoms) glycol (weight average molecular weight: 100 to 2000). Specific examples of them include hydroxyethyl(meth)acrylate, hydroxypropyl(meth)acrylate, triethyleneglycol(meth)acrylate, and poly-oxyethylene-oxypropylene mono(meth)allyl ether.

Examples of a water-soluble ethylenically unsaturated monomer having a carbamoyl group include (meth)acrylamide; N-alkyl (1 to 8 carbon atoms) (meth)acrylamides such as N-methyl acrylamide; N,N-dialkyl (alkyl having 1 to 8 carbon atoms) acrylamides such as N,N-dimethyl acrylamide and N,N-di-n- or i-propyl acrylamide; N-hydroxyalkyl (1 to 8 carbon atoms) (meth)acrylamides such as N-methylol(meth)acrylamide and N-hydroxyethyl(meth)acrylamide; and N,N-dihydroxyalkyl (1 to 8 carbon atoms) (meth)acrylamides such as N,N-dihydroxyethyl(meth)acrylamide. As an unsaturated monomer having a group composed of an amide, in addition to them, vinyl lactams having 5 to 10 carbon atoms (N-vinyl pyrrolidone, etc.) and the like can also be used.

Examples of a water-soluble ethylenically unsaturated monomer having an amino group include an amino group-containing ester of a mono-ethylenically unsaturated mono- or di-carboxylic acid and an amino group-containing amide of a mono-ethylenically unsaturated mono- or di-carboxylic acid. As the amino group-containing ester of a mono-ethylenically unsaturated mono- or di-carboxylic acid, dialkylaminoalkyl(meth)acrylate, di(hydroxyalkyl)aminoalkyl ester, morpholinoalkyl ester, and the like can be used, and examples thereof include dimethylaminoethyl(meth)acrylate, diethylamino(meth)acrylate, morpholinoethyl (meth)acrylate, dimethylaminoethyl fumarate, and dimethylaminoethyl malate. As the amino group-containing amide of a mono-ethylenically unsaturated mono- or di-carboxylic acid, monoalkyl(meth)acrylamide is preferred, and examples thereof include dimethylaminoethyl(meth)acrylamide and diethylaminoethyl(meth)acrylamide. As the water-soluble ethylenically unsaturated monomer having an amino group, in addition to them, vinylpyridines such as 4-vinylpyridine and 2-vinylpyridine can also be used.

The hydrolyzable monomer (a2) producing the water-soluble ethylenically unsaturated monomer (a1) by hydrolysis is not particularly limited, but an ethylenically unsaturated monomer having at least one hydrolyzable substituent that becomes a water-soluble substituent by hydrolysis is preferred. Examples of the hydrolyzable substituent include a group containing an acid anhydride, a group containing an ester linkage, and a cyano group.

As an ethylenically unsaturated monomer having a group containing an acid anhydride, an unsaturated dicarboxylic anhydride having 4 to 20 carbon atoms is used, and examples thereof include maleic anhydride, itaconic anhydride, and citraconic anhydride. Examples of an ethylenically unsaturated monomer having a group containing an ester linkage include lower alkyl esters of mono-ethylenically unsaturated carboxylic acids such as methyl(meth)acrylate and ethyl(meth)acrylate; and esters of mono-ethylenically unsaturated alcohols such as vinyl acetate and (meth)allyl acetate. Examples of an ethylenically unsaturated monomer having a cyano group include vinyl group-containing nitrile compounds having 3 to 6 carbon atoms such as (meth)acrylonitrile and 5-hexenenitrile.

As the water-soluble ethylenically unsaturated monomer (a1)) and the hydrolyzable monomer (a2), those described in Japanese Patent No. 3648553, Japanese Patent Publication No. 2003-165883, Japanese Patent Publication No. 2005-75982, and Japanese Patent Publication No. 2005-95759 can be further used. The water-soluble ethylenically unsaturated monomer (a1)) and the hydrolyzable monomer (a2) may be used alone or as a mixture of two or more kinds of monomers, respectively.

In addition to the water-soluble ethylenically unsaturated monomer (a1)) and the hydrolyzable monomer (a2), another vinyl monomer (a3) that is copolymerizable with these monomers can be used. As the copolymerizable other vinyl monomer (a3), hydrophobic vinyl monomers and the like can be used, but it is not limited to them. As the other vinyl monomer (a3), the following vinyl monomers (i) to (iii) and the like are used.

(i) Aromatic ethylenically unsaturated monomers having 8 to 30 carbon atoms;

Styrenes such as styrene, alpha-methylstyrene, vinyltoluene, and hydroxystyrene; vinylnaphthalene; and halogen substitutions of styrene such as dichlorostyrene.

(ii) Aliphatic ethylenically unsaturated monomers having 2 to 20 carbon atoms;

Alkenes such as ethylene, propylene, butene, isobutylene, pentene, heptene, diisobutylene, octene, dodecene, and octadecene; and alkadienes such as butadiene, and isoprene.

(iii) Alicyclic ethylenically unsaturated monomers having 5 to 15 carbon atoms;

Mono-ethylenically unsaturated monomers such as pinene, limonene, and indene; and polyethylenic vinyl-polymerizable monomers such as cyclopentadiene, bicyclopentadiene, and ethylidene norbornene.

As the other vinyl monomer (a3), those described in Japanese Patent No. 3648553, Japanese Publication No. 2003-165883, Japanese Patent Publication No. 2005-75982, and Japanese Patent Publication No. 2005-95759 can be further used.

From the aspect of providing the crosslinked polymer mainly composed of acrylic acid, as the water-soluble ethylenically unsaturated monomer (a1)) and/or the hydrolyzable monomer (a2) producing the water-soluble ethylenically unsaturated monomer (a1)) by hydrolysis, acrylic acid or a salt of acrylic acid (a1), or a hydrolyzable monomer (a2) producing acrylic acid or the salt of acrylic acid is preferable. The content of acrylic acid or the salt of acrylic acid (a1), or the hydrolyzable monomer (a2) producing acrylic acid or the salt of acrylic acid in the unsaturated monomer composition constituting the crosslinked polymer is preferably 90 mass % or more, more preferably 95 mass % or more, and is preferably 99 mass % or less, more preferably 97 mass % or less.

Examples of the internal crosslinking agent (b) can include an internal crosslinking agent (b1) having two or more ethylenically unsaturated groups, an internal crosslinking agent (b2) having: at least one functional group that can react with a water-soluble substituent of the water-soluble ethylenically unsaturated monomer (a1) and/or a water-soluble substituent produced by hydrolysis of the hydrolyzable monomer (a2); and at least one ethylenically unsaturated group, and an internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2).

Examples of the internal crosslinking agent (b1) having two or more ethylenically unsaturated groups include bis(meth)acrylamides having 8 to 12 carbon atoms, poly(meth)acrylates of polyols having 2 to 10 carbon atoms, polyallylamines having 2 to 10 carbon atoms, and poly(meth)allyl ethers of polyols having 2 to 10 carbon atoms. Specific examples of them include N,N'-methylene bis(meth)acrylamide, ethylene glycol di(meth)acrylate, poly (polymerization degree of 2 to 5) ethylene glycol di(meth)acrylate, propylene glycol di(meth)acrylate, glycerol (di or tri)acrylate, trimethylol propane triacrylate, diallylamine, triallylamine, triallylcyanurate, triallylisocyanurate, tetraallyloxyethane, pentaerythritol diallyl ether, pentaerythritol triallyl ether, pentaerythritol tetraallyl ether, and diglycerin di(meth)acrylate.

Examples of the internal crosslinking agent (b2) having at least one functional group that can react with a water-soluble substituent of the water-soluble ethylenically unsaturated monomer (a1) and/or a water-soluble substituent produced by hydrolysis of the hydrolyzable monomer (a2) and at least one ethylenically unsaturated group include ethylenically unsaturated compounds having 6 to 8 carbon atoms and an epoxy group, ethylenically unsaturated compounds having 4 to 8 carbon atoms and a hydroxyl group, and ethylenically unsaturated compounds having 4 to 8 carbon atoms and an isocyanato group. Specific examples of them include glycidyl(meth)acrylate, N-methylol(meth)acrylamide, hydroxyethyl(meth)acrylate, and isocyanato ethyl(meth)acrylate.

Examples of the internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2) can include polyhydric alcohols, polyvalent glycidyls, polyvalent amines, polyvalent aziridines, and polyvalent isocyanates. Examples of polyvalent glycidyl compounds include ethylene glycol diglycidyl ether and glycerin diglycidyl ether. Examples of polyvalent amine compounds include ethylenediamine, diethylenetriamine, triethylenetetramine, tetraethylenepentamine, pentaethylenehexamine, and polyethyleneimine. Examples of polyvalent aziridine compounds include Chemitite PZ-33 {2,2-bishydroxymethylbutanol-tris(3-(1-aziridinyl)propionate)}, Chemitite HZ-22 {1,6-hexamethylenediethyleneurea}, and Chemitite DZ-22 {diphenylmethane-bis-4,4'-N,N'-diethyleneurea}, available from Nippon Shokubai Co., Ltd. Examples of polyvalent polyisocyanate compounds include 2,4-tolylene diisocyanate and hexamethylene diisocyanate. These internal crosslinking agents may be used singly or two or more of them may be used in combination.

As the internal crosslinking agent (b), in light of absorbing performance (in particular, an absorption amount, an absorption speed, etc.), the internal crosslinking agent (b1) having two or more ethylenically unsaturated groups is preferred, poly(meth)allyl ethers of polyols having 2 to 10 carbon atoms are more preferred, triallylcyanurate, triallylisocyanurate, tetraallyloxyethane, or pentaerythritol triallyl ether is further preferred, and pentaerythritol triallyl ether is most preferred.

As the internal crosslinking agent (b), those described in Japanese Patent No. 3648553, Japanese Patent Publication No. 2003-165883, Japanese Patent Publication No. 2005-75982, and Japanese Patent Publication No. 2005-95759 can be further used.

As the method for polymerizing the crosslinked polymer (A), a conventionally known method and the like can be used, and a solution polymerization method, an emulsion polymerization method, a suspension polymerization method, and a reversed-phase suspension polymerization method can be used. In addition, a polymerization liquid at the polymerization may be in the form of a thin film, mist, or the like. As the method for controlling the polymerization, an adiabatic polymerization method, a temperature-controlled polymerization method, an isothermal polymerization method, and the like can be used. As the polymerization method, the solution polymerization method is preferred, and an aqueous solution polymerization method is more preferred since an organic solvent and the like are not used and it is advantageous in terms of production cost.

A water-containing gel {consisting of the crosslinked polymer and water} obtained by the polymerization can be chopped where necessary. The size (largest diameter) of the chopped gel is preferably from 50 micrometers to 10 cm, more preferably from 100 micrometers to 2 cm, and even more preferably from 1 mm to 1 cm. If the size falls within this range, dryability during a drying process becomes further favorable.

The chopping can be conducted by a known method, and can be conducted, for example, by using a conventional chopping apparatus such as a Bexmill, a rubber chopper, a Pharma Mill, a mincing machine, an impact type mill, and a roll type mill.

When a solvent (an organic solvent, water, etc.) is used for the polymerization, it is preferred to remove the solvent by distillation after the polymerization. When the solvent contains water, the water content (mass %) with respect to the mass (100 mass %) of the crosslinked polymer after the removal by distillation is preferably from 0 mass % to 20 mass %, more preferably from 1 mass % to 10 mass %, even more preferably from 2 mass % to 9 mass %, and most preferably from 3 mass % to 8 mass %. When the water content (% by mass) falls within the above range, the absorbing performance and the breakability of the water-absorbent resin powder after drying become further favorable.

It is noted that the content of the organic solvent and the water content are obtained based on a decrease in the mass of a measurement sample from before heating to after heating by an infrared moisture measuring instrument {JE400 manufactured by Kett Electric Laboratory or the like: 120 plus or minus 5 degrees centigrade, 30 minutes, an atmospheric humidity before heating of 50 plus or minus 10% RH, lamp specifications of 100 V and 40 W}.

As the method for removing the solvent (including water) by distillation, a method in which removal by distillation (drying) is conducted by hot air at a temperature in a range from 80 degrees centigrade to 230 degrees centigrade, a thin film drying method with a drum dryer or the like heated at the temperature in a range from 100 degrees centigrade to 230 degrees centigrade, a (heating) reduced-pressure drying method, a freeze-drying method, a drying method with infrared rays, decantation, filtration, and the like can be used.

The crosslinked polymer (A) can be pulverized after being dried. The pulverizing method is not particularly limited, and, for example, an ordinary pulverizing apparatus such as a hammer type pulverizer, an impact type pulverizer, a roll type pulverizer, and a jet streaming type pulverizer can be used. The particle size of the pulverized crosslinked polymer (A) can be adjusted by sieving or the like where necessary.

The weight average particle size (micrometer) of the crosslinked polymer (A) that is sieved where necessary is preferably from 100 micrometers to 800 micrometers, more preferably from 200 micrometers to 700 micrometers, even more preferably from 250 micrometers to 600 micrometers, particularly preferably from 300 micrometers to 500 micrometers, and most preferably from 350 micrometers to 450 micrometers. When the weight average particle size (micrometer) of the crosslinked polymer (A) falls within the above range, the absorbing performance becomes further favorable.

It is noted that the weight average particle size is measured with a ro-tap test sieve shaker and standard sieves (JIS Z8801-1: 2006) according to the method described in Perry's Chemical Engineers Handbook, Sixth Edition (The McGraw-Hill Companies, 1984, Page 21). In other words, as JIS standard sieves, for example, sieves of 1000 micrometers, 850 micrometers, 710 micrometers, 500 micrometers, 425 micrometers, 355 micrometers, 250 micrometers, 150 micrometers, 125 micrometers, 75 micrometers, and 45 micrometers, and a tray are combined in order from above. About 50 g of a measurement particle is placed into the uppermost sieve, and shaken with the ro-tap test sieve shaker for 5 minutes. The weights of the measurement particles on each sieve and the tray are measured, and the weight fraction of the particles on each sieve is obtained with the total weight regarded as 100% by weight. The values are plotted in a log probability paper {the horizontal axis is used for the opening of the sieve (particle size) and the vertical axis is used for the weight fraction}, then a line is drawn so as to connect each point, and a particle size corresponding to 50% by mass of the mass fraction is obtained and regarded as a weight average particle size.

The surface of the crosslinked polymer (A) may be treated with the surface modifier (B). Examples of the surface modifier (B) include polyvalent metal compounds such as aluminum sulfate, potassium alum, ammonium alum, sodium alum, (poly) aluminum chloride, and hydrates thereof; polycation compounds such as polyethyleneimine, polyvinylamine, and polyallylamine; inorganic fine particles; a surface modifier (B1) containing a hydrocarbon group; a surface modifier (B2) containing a hydrocarbon group having a fluorine atom; and a surface modifier (B3) having a polysiloxane structure.

Examples of the inorganic fine particles include oxides such as silicon oxide (silica), aluminum oxide (alumina), iron oxide, titanium oxide, magnesium oxide, and zirconium oxide, carbides such as silicon carbide and aluminum carbide, nitrides such as titanium nitride, and complexes thereof (e.g., zeolite, talc, etc.). Among them, oxides are preferred, and silicon oxide is further preferred. The volume average particle size of the inorganic fine particles is preferably from 10 nm to 5000 nm, more preferably from 30 nm to 1000 nm, even more preferably from 50 nm to 750 nm, and most preferably from 90 nm to 500 nm. It is noted that the volume average particle size is measured in a solvent by a dynamic light scattering method. Specifically, the volume average particle size is measured in cyclohexane as a solvent at a temperature of 25 degrees centigrade by using the nano track particle size distribution measuring instrument UPA-EX150 (light source: He—Ne laser) manufactured by Nikkiso Co., Ltd.

Examples of the surface modifier (B1) containing a hydrocarbon group include polyolefin resins, polyolefin resin derivatives, polystyrene resins, polystyrene resin derivatives, waxes, long-chain fatty acid esters, long-chain fatty acids and salts thereof, long-chain aliphatic alcohols, and mixtures of two or more of them.

Examples of the surface modifier (B2) containing a hydrocarbon group having a fluorine atom include perfluoroalkanes, perfluoroalkenes, perfluoroaryls, perfluoroalkyl ethers, perfluoroalkylcarboxylic acids or salts thereof, perfluoroalkyl alcohols, and mixtures of two or more of them.

Examples of the surface modifier (B3) having a polysiloxane structure include polydimethylsiloxane; polyethermodified polysiloxanes such as polyoxyethylene-modified polysiloxane and poly(oxyethylene/oxypropylene)-modified polysiloxane; carboxy-modified polysiloxanes; epoxy-modified polysiloxanes; amino-modified polysiloxanes; alkoxy-modified polysiloxanes; and mixtures thereof.

As the surface modifier (B), in light of absorption properties, the surface modifier (B3) having a polysiloxane structure and inorganic fine particles are preferred, and amino-modified polysiloxanes, carboxy-modified polysiloxanes, and silica are more preferred.

The method for treating the crosslinked polymer (A) with the surface modifier (B) is not particularly limited, as long as treatment is conducted such that the surface modifier (B) is present on the surface of the crosslinked polymer (A). However, from the standpoint that the amount of the surface modifier (B) on the surface is controlled, it is preferred that the surface modifier (B) is mixed with a dried product of the crosslinked polymer (A), not with a water-containing gel of the crosslinked polymer (A) or a polymerization liquid that is prior to polymerization of the crosslinked polymer (A). It is noted that it is preferred that the mixing is uniformly conducted.

The shape of the water-absorbent resin powder is not particularly limited, and examples thereof include an indefinite crushed shape, a scale shape, a pearl shape, a rice grain shape, or the like. Among them, the indefinite crushed shape is preferred from the standpoint that the powder in such a shape can be well entangled with fibrous materials in applications such as a disposable diaper and there is little possibility of the powder falling off from the fibrous materials.

The water-absorbent resin powder can be subjected to surface crosslinking where necessary. As a crosslinking agent for conducting the surface crosslinking (a surface crosslinking agent), the same ones as the internal crosslinking agent (b) can be used. In light of absorption performance and the like of the water-absorbent resin powder, the surface crosslinking agent is preferably the crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2), more preferably a polyvalent glycidyl, even more preferably ethylene glycol diglycidyl ether and glycerin diglycidyl ether, and most preferably ethylene glycol diglycidyl ether.

In the case of conducting the surface crosslinking, the content (mass %) of the surface crosslinking agent with respect to the total mass (100 mass %) of the water-soluble ethylenically unsaturated monomer (a1) and/or the hydrolyzable monomer (a2), the internal crosslinking agent (b), and the other vinyl monomer (a3) used where necessary is preferably from 0.001 mass % to 7 mass %, more preferably from 0.002 mass % to 5 mass %, and even more preferably 0.003 mass % to 4 mass %. In other words, in this case, the upper limit of the content of the surface crosslinking agent based on the total mass of (a1) and/or (a2), (b), and (a3) is preferably 7 mass %, more preferably 5 mass %, and even more preferably 4 mass %. Similarly, the lower limit is preferably 0.001 mass %, more preferably 0.002 mass %, and even more preferably 0.003 mass %. If the content of the surface crosslinking agent falls within the above range, the absorption performance becomes further favorable. The surface crosslinking can be achieved by, for example, a method of spraying an aqueous solution containing the surface crosslinking agent to the water-absorbent resin powder or impregnating the water-absorbent resin powder with the aqueous solution containing the surface crosslinking agent, followed by heating treatment (100 to 200 degrees centigrade) on the water-absorbent resin powder.

The water-absorbent resin powder can contain additives such as an antiseptic, a fungicide, an antibacterial, an antioxidant, a ultraviolet absorber, a coloring agent, a perfuming agent, a deodorizer, an inorganic powder, and an organic fibrous material. Examples of such additives include those exemplified in Japanese Patent Publication No. 2003-225565 and Japanese Patent Publication No. 2006-131767. When these additives are contained, the content (mass %) of the additives with respect to the crosslinked polymer (A) (100 mass %) is preferably from 0.001 mass % to 10 mass %, more preferably from 0.01 mass % to 5 mass %, even more preferably from 0.05 mass % to 1 mass %, and most preferably from 0.1 mass % to 0.5 mass %.

The absorption ratio of the water absorbent resin powder is preferably 50 g/g or more, more preferably 53 g/g or more, and further preferably 55 g/g or more, and is preferably 70 g/g or less, more preferably 65 g/g or less, and further preferably 60 g/g or less. When the absorption ratio is 50 g/g or more, absorptive capacity can be maintained at a predetermined level with a small amount of the water absorbent resin powder, and it becomes easy to manufacture a thin absorbent body. From a standpoint of preventing liquid leakage, an absorption ratio is preferably as large as possible. However, when the absorption ratio is 70 g/g or less, the stability of the water absorbent resin powder against urine is improved.

The water retention amount of the water absorbent resin powder is preferably 25 g/g or more, more preferably 27 g/g or more, and even more preferably 30 g/g or more, further preferably 40 g/g or more, and is preferably 60 g/g or less, more preferably 57 g/g or less, and further preferably 55 g/g or less. When the water retention amount is 25 g/g or more, body fluid retention volume can be maintained at a predetermined level with a small amount of the water absorbent resin powder, and it becomes easy to manufacture a thin absorbent body. From a standpoint of preventing liquid leakage, a water retention amount is preferably as large as possible. However, when the water retention amount is 60 g/g or less, the stability of the water absorbent resin powder against urine is improved.

Diffusibility Improvement Material

Next, the diffusibility improvement material used in the present invention will be described. The diffusibility improvement material is a material for improving the diffusibility of the body fluid or the like in the absorbent body, especially a material for improving the diffusibility under the load. The diffusibility improvement material preferably has an under-load liquid passing rate of 15 seconds or less, more preferably 12 seconds or less, even more preferably 10 seconds or less, further more preferably 8 seconds or less. If the diffusibility improvement material has an under-load liquid passing rate of 15 seconds or less, the puddle of the liquid after excretion is suppressed. It is noted that the method for measuring the under-load liquid passing rate of the diffusibility improvement material is described later.

The form of the diffusibility improvement material is not particularly limited, and examples thereof include a granular form, a sheet-like form, and the like. Examples of a granular diffusibility improvement material include resin particles such as polypropylene particles, polystyrene particles, and ABS (acrylonitrile-butadiene-styrene copolymer) resin particles. It should be noted that these resin particles do not substantially have any water absorptivity.

The particle diameter of the granular diffusibility improvement material is preferably 0.05 mm or more, more preferably 0.1 mm or more, further preferably 0.8 mm or more, and is preferably 10 mm or less, more preferably 7 mm or less, and further preferably 6 mm or less. If the particle diameter is within the above described range, the diffusibility of body fluid or the like becomes excellent and the uncomfortable feeling when wearing is reduced.

Examples of a sheet-like diffusibility improvement material include a three-dimensional structural body having a void. Examples of such three-dimensional structural body include: natural products such as a dried sponge-gourd; a three-dimensional interlaced body of a resin fiber (e.g., BREATHAIR (Registered trademark) manufactured by Toyobo Co., Ltd.); and a three-dimensional stereo knitted goods of a resin fiber (e.g., Fusion (Registered trademark) manufactured by Asahi Kasei Fibers Corp.). It should be noted that since nonwoven fabrics and the like conventionally used for an absorbent article have thin fibers, void included therein will be crushed when a load is applied. This results in an under-load liquid passing rate larger than 15 seconds, which does not qualify as a diffusibility improvement material that is to be used in the present invention.

Configuration of Absorbent Body

The configuration of the absorbent body of the present invention, having at least two or more layers, includes: a water absorption layer having a water absorption region where a water absorbent resin powder is disposed, and a thickness-direction-penetrating opening region; and, as a lower layer of the water absorption layer, a layer having a diffusion region where a diffusibility improvement material having an under-load liquid passing rate of 15 seconds or less is disposed. The lower layer has the diffusion region disposed at least a part of a portion located below the opening region.

The water absorption layer has the water absorption region and the opening region. The water absorption region is composed of a water absorbent material such as a water absorbent resin powder or a water absorbent fiber. Examples of the water absorbent fiber include pulp fibers, cellulose fibers, rayon, and acetate fibers. The water absorption region may include a fiber base-material in addition to a water absorbent resin powder. Examples of the fiber base-material include thermal bonding fibers and the like. Thermal bonding fibers are used to enhance shape retention. Specific examples of the thermal bonding fibers include polyolefin fibers such as polyethylene and polypropylene, polyester fibers, and composite fibers.

The opening region is a portion where the water absorbent resin powder is not disposed in the water absorption layer. As long as the opening region penetrates the water absorption layer in its thickness direction, the size and shape of the opening region is not particularly limited. Examples of the planar view shape of the opening region include a circular shape, an elliptical shape, a polygonal shape (e.g., rectangular shape, triangular shape), a polygonal shape having rounded corners (the shape of a polygon whose vertices are rounded), a slit shape (e.g., linear slit, wavy slit), and the like. Furthermore, the number of the opening region is not particularly limited, and a single or multiple (two or more) opening regions may be formed.

When only a single opening region is formed, the opening region is preferably formed so as to span over the central line of the absorbent body in the width direction. Furthermore, when the planar view shape of the opening region is an elliptical shape or a rectangular shape, the longitudinal axis direction or long side direction thereof is preferably parallel or approximately parallel with the longitudinal direction of the water absorption layer. When the opening region has a slit shape, the longitudinal direction of the slit is preferably parallel or approximately parallel with the longitudinal direction of the water absorption layer.

When multiple opening regions are formed, their arrangements are not particularly limited. Examples of the arrangements of the opening regions whose planar view shapes are a circular shape, an elliptical shape, a polygonal shape (e.g., rectangular shape), or a polygonal shape having rounded corners include an alternate pattern, and a grid pattern. Examples of the arrangements of the slit shaped opening regions include a mode in which the slit shaped opening regions are arranged parallel to each other, and a mode in which the slit shaped opening regions are arranged so as to intersect with each other.

In the water absorption layer, the area ratio of the opening region with respect to the surface of water absorption layer is preferably 5% or more, more preferably 20% or more, and further preferably 40% or more, and preferably 70% or less, more preferably 60% or less, and further preferably 50% or less. When the area ratio is 5% or more, body fluid or the like is easily taken into the diffusion region and diffusibility is further improved. When the area ratio is 70% or less, the area ratio of the water absorption region becomes relatively large, and the water absorption amount becomes large.

The water absorption layer may be formed by fixing the water absorbent material or the like to a paper sheet such as tissue paper or a liquid-permeable nonwoven fabric sheet, or by wrapping the water absorbent material with a paper sheet such as tissue paper or a liquid-permeable nonwoven fabric sheet, and molding the wrapped product into a desired shape. It should be noted that when using a paper sheet or a liquid-permeable nonwoven fabric sheet, these sheets may be disposed on the upper side and/or lower side of the opening region, or portions corresponding to the opening regions of these sheets may be cut out.

Examples of the layer having the diffusion region where a diffusibility improvement material having an under-load liquid passing rate of 15 seconds or less is disposed include: a diffusion layer only having a diffusion region; and a water diffusion-and-absorption layer having a diffusion region and a water absorption region.

The diffusion layer mainly has a function of diffusing body fluid or the like. When the diffusion layer is formed from a sheet-like diffusibility improvement material, its thickness is preferably 0.5 mm or more, more preferably 2 mm or more, and further preferably 2.5 mm or more, and is preferably 15 mm or less, more preferably 10 mm or less, and further preferably 7 mm or less. When the thickness of the diffusion layer formed from the sheet-like diffusibility improvement material is within the above described range, diffusibility can be improved without impairing the texture. When the diffusion layer is formed from a particulate diffusibility improvement material, its thickness is preferably 0.05 mm or more, more preferably 0.1 mm or more, and further preferably 0.15 mm or more, and is preferably 10 mm or less, more preferably 7 mm or less, and further preferably 6 mm or less. When the thickness of the diffusion layer formed from the particulate diffusibility improvement material is within the above described range, diffusibility can be improved without impairing the texture.

The planar view shape of the diffusion layer may be substantially identical to the planar view shape of the water absorption layer having the opening region, and may be smaller than the planar view shape of the water absorption layer. Although the diffusion layer may be disposed at least part of a portion located below the opening region of the water absorption layer, the diffusion layer is preferably disposed on the whole region below the opening region. The diffusion layer is preferably formed so as to extend below the water absorption region adjacent to the opening region.

The area ratio of the diffusion layer with respect to the planar view shape of the water absorption layer having the opening region arranged immediately above the diffusion layer is preferably not lower than 5%, more preferably not lower than 15%, and further preferably not lower than 20%. When the area ratio of the diffusion layer is not lower than 5%, the diffusibility is further improved, and the absorption rate of the body fluid or the like becomes faster. The upper limit of the area ratio of the diffusion layer is, but not particularly limited to, 100%.

The water diffusion-and-absorption layer has the functions of diffusing body fluid or the like by the diffusion region in the thickness direction and the planar direction of the layer, and absorbing body fluid by the water absorption region. In the water diffusion-and-absorption layer, the size and shape of the diffusion region is not particularly limited. Examples of the planar view shape of the diffusion region on the surface of the water diffusion-and-absorption layer include a circular shape, an elliptical shape, a polygonal shape (e.g., rectangular shape, triangular shape), a polygonal shape having rounded corners (shape of a polygon whose vertices are rounded), and a slit shape (e.g., linear slit, wavy slit). Furthermore, the number of the diffusion region is not particularly limited, and a single or multiple (two or more) diffusion regions may be formed.

The diffusion region and the water absorption region may be formed by fixing the diffusibility improvement material, the water absorbent material, and the like to a paper sheet such as tissue paper, or a liquid-permeable nonwoven fabric sheet; or by wrapping the diffusibility improvement material, the water absorbent material, and the like with a paper sheet such as tissue paper, or a liquid-permeable nonwoven fabric sheet, and molding the wrapped product into a desired shape.

In the absorbent body of the present invention, the lower layer has the diffusion region disposed at least a part of a portion located below the opening region. In other words, when the absorbent body is planarly viewed from the skin surface (top surface) side, the diffusion region is disposed at a part of the lower side (external surface side) of the opening region. On the lower layer, the diffusion region is preferably disposed on the whole portion located below the opening region. Furthermore, although the planar view shape of the opening region and the planar view shape of the diffusion region disposed below the opening region may be substantially identical, the planar view shape of the diffusion region is preferably larger. That is, the diffusion region provided below the opening region preferably extends to below the water absorption region adjacent to the opening region. By having such a configuration, the body fluid or the like taken into the diffusion region is easily absorbed on the bottom surface (external surface) side of the water absorption region through the diffusion region.

In the water diffusion-and-absorption layer, the area ratio of the diffusion region with respect to the surface of the water diffusion-and-absorption layer is preferably 5% or more, more preferably 15% or more, and further preferably 20% or more, and is preferably 70% or less, more preferably 50% or less, and further preferably 40% or less. When the area ratio is 5% or more, the absorption rate of body fluid or the like is further improved, and when the area ratio is 70% or less, the area ratio of the water absorption region becomes relatively large and the water absorption amount becomes large.

Similar to the diffusion layer, the thickness of the diffusion region portion of the water diffusion-and-absorption layer can be appropriately adjusted in accordance with the material forming the diffusion region. When a sheet-like diffusibility improvement material and a particulate diffusibility improvement material are used, the suitable range for the thickness of the diffusion region is similar to that for the diffusion layer.

In the absorbent body of the present invention, the shapes of the diffusion layer, the water diffusion-and-absorption layer, and the water absorption layer are not particularly limited, and examples thereof include a rectangular shape, an hourglass shape, a gourd shape, a battledore shape, and the like. The absorbent body may further have, on the lower side (external surface side) of the diffusion layer and the water diffusion-and-absorption layer, a water absorption layer that does not have an opening region. By having such a water absorption layer, the water retention amount of the absorbent body is further improved. Furthermore, in addition to the diffusion layer, the water diffusion-and-absorption layer, and the water absorption layer; the absorbent body may include a nonwoven fabric layer, and an adhesive layer for fixing the diffusibility improvement material and the water absorbent resin powder.

In addition, an impermeable sheet may be disposed on the lowermost side of the absorbent body. As the impermeable sheet, for example, a water-repellent or liquid impermeable nonwoven fabric (e.g., a spunbond nonwoven fabric, a meltblown nonwoven fabric, and an SMS (spunbond-meltblown-spunbond) nonwoven fabric) formed from a hydrophobic fiber (e.g., polypropylene, polyethylene, polyester, polyamide, and nylon) or a water-repellent or liquid impermeable plastic film is used for preventing moisture and the like of excrement that reaches the impermeable sheet from oozing out the absorbent article. When a plastic film is used as the impermeable sheet, a plastic film having moisture permeability (breathability) is preferably used from a standpoint of improving a wearer's comfort by preventing dampness.

Examples of the configuration of the absorbent body of the present invention include: (1) a configuration having a diffusion layer and a water absorption layer including an opening region, wherein the diffusion layer is disposed at least a part of a portion located below the opening region; and (2) a configuration having a water absorption layer including an opening region, and a water diffusion-and-absorption layer having a diffusion region and a water absorption region, wherein the diffusion region is disposed on the water diffusion-and-absorption layer at least a part of a portion located below the opening region.

In the configuration of (1) described above, the planar view shape of the diffusion layer may be substantially identical to the planar view shape of the water absorption layer including the opening region, and may be smaller than the planar view shape of the water absorption layer. Although the diffusion layer may be disposed at least a part of a portion located below the opening region of the water absorption layer, the diffusion layer is preferably disposed on the whole region below the opening region. The diffusion layer is preferably formed so as to extend below the water absorption region adjacent to the opening region. Furthermore, in the configuration of (1) described above, a water absorption layer not having an opening region may be included below (external surface side) the diffusion layer. The water retention amount of the absorbent body is further improved by having such a water absorption layer.

In the configuration of (2) described above, the planar view shape of the water diffusion-and-absorption layer may be substantially identical to the planar view shape of the water absorption layer including the opening region, and may be smaller than the planar view shape of the water absorption layer. In the water diffusion-and-absorption layer, although the diffusion region may be disposed at least a part of a portion located below the opening region of the water absorption layer, the diffusion layer is preferably disposed on the whole region below the opening region. The diffusion region is preferably formed so as to extend below the water absorption region adjacent to the opening region. Furthermore, in the configuration of (2) described above, a water absorption layer not having an opening region may be included below (external surface side) the water diffusion-and-absorption layer. The water retention amount of the absorbent body is further improved by having such a water absorption layer.

In the configurations of (1) and (2) described above, the absorbent body may have multiple layers of both the water absorption layer including the opening region, and the diffusion layer or the water diffusion-and-absorption layer. When there are multiple water absorption layers, at least a water absorption layer (hereinafter, uppermost water absorption layer) disposed at the uppermost side (skin side) includes an opening region. Furthermore, when the diffusion layer is disposed immediately below (external surface side) the uppermost water absorption layer, the diffusion layer is disposed at least a part of a portion located below the opening region. Furthermore, when the water diffusion-and-absorption layer is disposed immediately below the uppermost water absorption layer, the diffusion region is disposed on the water diffusion-and-absorption layer at least a part of a portion located below the opening region.

When there are multiple water absorption layers, the water absorption layers other than the uppermost water absorption layer do not need to include an opening region. However, from a standpoint of improving the water absorption rate, the water absorption layer disposed on the upper side (skin surface side) of the diffusion layer or the water diffusion-and-absorption layer preferably includes an opening region. In addition, on the water diffusion-and-absorption layer or the diffusion layer disposed immediately below (external surface side) the water absorption layer including the opening region, the diffusion region is preferably disposed at least a part of a portion located below the opening region. When there are multiple water absorption layers having opening regions, the positions, sizes, and number of the opening regions formed thereon may be the same or different from each other.

In the following, although description of a preferable embodiment of the absorbent body of the present invention will be provided with reference to the drawings, the present invention is not limited to the mode that has been diagrammatically represented.

Specific examples of how the opening regions are formed in the water absorption layer will be described with reference to FIG. 7. FIG. 7 is a plan view of a water absorption layer from a skin surface side, reference character "2" indicates a water absorption region, reference character "3" indicates an opening region, and a dot and dash line "L" indicates the central line of the water absorption layer in the width direction. It should be noted that a shaded portion in the figure is an opening region. Examples of the mode of the water absorption layer including an opening region include: a mode ((a) of FIG. 7) in which a single linear-slit shaped opening region 3 is formed; a mode ((b) of FIG. 7) in which a single wavy-slit shaped opening region 3 is formed; a mode ((c) of FIG. 7) in which a plurality of circular shaped opening regions 3 are formed in a grid-pattern arrangement; a mode ((d) of FIG. 7) in which a plurality of circular shaped opening regions 3 are formed in an alternate arrangement; a mode ((e) of FIG. 7) in which a plurality of linear slit shaped opening regions 3 are formed parallel to each other; and a mode ((f) of FIG. 7) in which a plurality of wavy slit shaped opening regions 3 are formed parallel to each other. It should be noted that, in (a) to (d) of FIG. 7, the opening region 3 is formed so as to span over a central line L of the water absorption layer in the width direction.

Examples of a preferable embodiment of the absorbent body of the present invention include: a mode with a single diffusion layer and a single water absorption layer including an opening region, wherein the diffusion layer is disposed at least a part of a portion located below the opening region (Embodiment 1); a mode with a single water absorption layer including an opening region and a single water diffusion-and-absorption layer having a diffusion region and a water absorption region, wherein the diffusion region is disposed on the water diffusion-and-absorption layer at least a part of a portion located below the opening region (Embodiment 2); and a mode with two diffusion layers and two water absorption layers including opening regions, wherein each of the diffusion layers is disposed at least a part of a portion located below an opening region of a water absorption layer disposed immediately above each of the diffusion layers (Embodiment 3).

FIGS. 1 and 2 are schematic diagrams showing Embodiment 1 of the absorbent body of the present invention. FIG. 1 is a perspective view from a skin surface side, and FIG. 2 is a cross sectional view along line X-X in FIG. 1. FIGS. 3 and 4 are schematic diagrams showing Embodiment 2 of the absorbent body of the present invention. FIG. 3 is a perspective view from a skin surface side, and FIG. 4 is a cross sectional view along line Y-Y in FIG. 3. FIGS. 5 and 6 are schematic diagrams showing Embodiment 3 of the absorbent body of the present invention. FIG. 5 is a perspective view from a skin surface side, and FIG. 6 is a cross sectional view along line Z-Z in FIG. 5. It should be noted that, in FIGS. 1 to 6, with respect to C direction on the paper surface, the upper side is the skin surface side, whereas the lower side is the external surface side.

Embodiment 1

Embodiment 1 is an absorbent body 1 composed of two layers, i.e., a water absorption layer 4 including water absorption regions 2 and an opening region 3, and a diffusion layer 5 disposed below the water absorption layer 4.

In the absorbent body 1 shown in FIG. 1, the water absorption layer 4 and the diffusion layer 5 both have a rectangular shape with a longitudinal direction A and a short direction B, and the planar view shapes of the water absorption layer 4 and the diffusion layer 5 are substantially identical. Thus, the diffusion layer 5 is disposed across the whole region below the opening region 3 and the water absorption regions 2. On the water absorption layer 4, the linear slit shaped opening region 3 extending in the longitudinal direction of the absorbent body is singly formed, and the water absorption regions 2 are formed on both sides thereof in the width direction. The opening region 3 is formed so as span over a central line L of the absorbent body 1 (water absorption layer 4) in the width direction B, and is formed such that the longitudinal direction of the slit and the longitudinal direction A of the absorbent body 1 are parallel or approximately parallel to each other.

In FIG. 1, although a rectangular shape is diagrammatically represented as the shapes of the water absorption layer 4 and the diffusion layer 5, the shapes of those may be an hourglass shape, a gourd shape, a battledore shape, or the like. In addition, the planar view shape of the diffusion layer 5 may be smaller than the planar view shape of the water absorption layer 4. However, it is necessary to dispose the diffusion layer 5 at least a part of a portion located below the opening region 3. In the mode diagrammatically represented in FIG. 1, although the linear slit shaped opening region 3 is singly formed on the water absorption layer 4, the number of slits may be two or more. In addition, the shape of the slit may be a curved line such as a wavy line. In FIG. 1, although the absorbent body including two layers of the water absorption layer 4 and the diffusion layer 5 is diagrammatically represented, a nonwoven fabric layer or an adhesive layer may be inserted between the water absorption layer 4 and the diffusion layer 5. Furthermore, a water absorption layer not having an opening region may be disposed below the diffusion layer 5.

Embodiment 2

Embodiment 2 is an absorbent body 1 composed of two layers, i.e., a water absorption layer 4 including water absorption regions 2 and an opening region 3, and a water diffusion-and-absorption layer 7 having formed thereon a slit shaped diffusion region 6 disposed below the water absorption layer 4.

In the absorbent body 1 shown in FIG. 3, the water absorption layer 4 and the water diffusion-and-absorption layer 7 both have a rectangular shape with a longitudinal direction A and a short direction B, and the planar view shapes of the water absorption layer 4 and the water diffusion-and-absorption layer 7 are substantially identical. On the water absorption layer 4, the linear slit shaped opening region 3 extending in the longitudinal direction of the absorbent body is singly formed, and the water absorption regions 2 are formed on both sides thereof in the width direction. The opening region 3 is formed so as to span over a central line L of the absorbent body 1 (the water absorption layer 4) in the width direction B, and is formed such that the longitudinal direction of the slit and the longitudinal direction A of the absorbent body 1 are parallel or approximately parallel to each other.

On the water diffusion-and-absorption layer 7, the diffusion region 6 is formed at a portion located below the opening region 3. The diffusion region 6 is formed so as to be wider than the opening region 3, and is formed so as to extend below the water absorption regions 2 adjacent to the opening region 3.

In FIG. 3, although a rectangular shape is diagrammatically represented as the shapes of the water absorption layer 4 and the water diffusion-and-absorption layer 7, the shapes may be an hourglass shape, a gourd shape, a battledore shape, or the like. In addition, the planar view shape of the water diffusion-and-absorption layer 7 may be smaller or larger than that of the water absorption layer 4. In FIG. 3, although a mode in which the linear slit shaped opening region 3 is singly formed on the water absorption layer 4 is diagrammatically represented, the number of the slits may be two or more. Furthermore, the shape of the slit may be a curved line such as a wavy line. In FIG. 3, although the absorbent body composed of two layers of the water absorption layer 4 and the water diffusion-and-absorption layer 7 is diagrammatically represented, a nonwoven fabric layer or an adhesive layer may be inserted between the water absorption layer 4 and the water diffusion-and-absorption layer 7. In addition, a water absorption layer not having an opening region may be disposed below the water diffusion-and-absorption layer.

Embodiment 3

Embodiment 3 is an absorbent body 1 composed of four layers: a first water absorption layer 41 including water absorption regions 21 and an opening region 31; a first diffusion layer 51 disposed below the first water absorption layer 41; a second water absorption layer 42 including an opening region 32 and water absorption regions 22 disposed below the first diffusion layer 51; and a second diffusion layer 52 disposed below the second water absorption layer 42.

In the absorbent body 1 diagrammatically represented in FIG. 5, the first water absorption layer 41, the second water absorption layer 42, the first diffusion layer 51, and the second diffusion layer 52 all have a rectangular shape with a longitudinal direction A and a short direction B, and the planar view shapes of all the layers are substantially identical. Thus, the first diffusion layer 51 is disposed across the whole region below the water absorption regions 21 and the opening region 31 of the first water absorption layer 41. Furthermore, the second diffusion layer 52 is disposed across the whole region below the water absorption regions 22 and the opening region 32 of the second water absorption layer 42.

On the first water absorption layer 41 and the second water absorption layer 42, the linear slit shaped opening regions 31 and 32 extending in the longitudinal direction of the absorbent body are respectively formed singly, and the water absorption regions 21 and 22 are formed on both sides of those in the width direction. The opening regions 31 and 32 included in the first water absorption layer 41 and the second water absorption layer 42 are both formed so as to span over a central line L of the absorbent body 1 (the first water absorption layer 41 or the second water absorption layer 42) in the width direction B, and are formed such that the longitudinal direction of the slits and the longitudinal direction A of the absorbent body 1 are parallel or approximately parallel to each other. In addition, the planar view shapes of the opening regions 31 and 32 are formed substantially identical to each other, and their formed positions are also substantially identical to each other.

In FIG. 5, although a rectangular shape is diagrammatically represented as the shapes of the first water absorption layer 41, the second water absorption layer 42, the first diffusion layer 51, and the second diffusion layer 52; these shapes may be an hourglass shape, a gourd shape, a battledore shape, or the like. In addition, the planar view shape of the first diffusion layer 51 may be smaller than the planar view shape of the first water absorption layer 41, and the planar view shape of the second diffusion layer 52 may be smaller than the planar view shape of the second water absorption layer 42. However, it is necessary to dispose the first diffusion layer 51 at least a part of a portion located below the opening region 31, and dispose the second diffusion layer 52 at least a part of a portion located below the opening region 32. In FIG. 5, although a mode in which the linear slit shaped opening regions 31 and 32 are respectively formed singly on the first water absorption layer 41 and the second water absorption layer 42 is diagrammatically represented, the number of slits may be two or more. In addition, the shapes of the slits may be a curved line such as a wavy line. In FIG. 5, although the absorbent body composed of four layers, i.e., the first water absorption layer 41, the second water absorption layer 42, the first diffusion layer 51, and the second diffusion layer 52, is diagrammatically represented; a nonwoven fabric layer or an adhesive layer may be inserted between each of the layers. Furthermore, a water absorption layer not having an opening region may be disposed below the second diffusion layer 52.

Absorbent Article

Next, description of a specific application example of the absorbent article of the present invention will be provided. Examples of the absorbent article of the present invention include absorbent articles used for absorbing body fluid discharged from the human body, such as an incontinence pad, a disposable diaper, a sanitary napkin, and a breast-milk pad.

When the absorbent article is an incontinence pad or a sanitary napkin, for example, the absorbent body is disposed between the top sheet and the back sheet. Examples of the shape of the incontinence pad or the sanitary napkin include a substantially rectangular shape, an hourglass shape, a gourd shape, and the like.

When the absorbent article is a disposable diaper, examples of the disposable diaper include: a tape-type disposable diaper that has one pair of securing members on right and left sides of a back portion or a front abdominal portion, and that forms, because of the securing member, a pants shape when being worn; and a pants-type disposable diaper having a waist opening and one pair of leg openings formed when a front abdominal portion and a back portion are joined together.

When the absorbent article is a disposable diaper, in the disposable diaper, for example, a laminated body including an inner sheet and an outer sheet may form a diaper main body including a front abdominal portion, a back portion, and a crotch portion located between those, and the absorbent body may be disposed on the crotch portion between the top sheet and the back sheet. Furthermore, the disposable diaper may include, for example, a laminated body having the absorbent body disposed between a top sheet and a back sheet, and the laminated body may include a front abdominal portion, a back portion, and a crotch portion located between those. It should be noted that, with regard to the front abdominal portion, the back portion, and the crotch portion, when the disposable diaper is worn, a portion placed on the abdominal side of a wearer is referred to as a front abdominal portion, a portion placed on the hip side of the wearer is referred to as a back portion, and a portion located between the front abdominal portion and the back portion and placed on the crotch of the wearer is referred to as a crotch portion. The inner sheet is preferably hydrophilic or water-repellent, and the outer sheet is preferably water-repellent.

The absorbent article preferably has rise flaps disposed along both side-edge portions of the absorbent body. For example, the rise flaps may be disposed on both side-edge portions of the top surface of the absorbent body in the width direction, or may be disposed on both outer sides of the absorbent body in the width direction. By providing the rise flaps, side-leakage of excrement such as urine can be prevented. The rise flaps may be formed by causing, to rise, inward edges of side sheets provided on both sides of the top sheet in the width direction. The rise flap and the side sheets are preferably water-repellent.

Next, using an incontinence pad as an example, the absorbent article of the present invention will be described with reference to FIGS. 8 and 9. FIG. 8 shows a plan view of an incontinence pad. FIG. 9 is a cross sectional view of an incontinence pad along V-V in FIG. 8. It should be noted that, in the figure, arrow B is defined as the width direction, and arrow A is defined as the longitudinal direction. Furthermore, a direction on the surface formed by arrows A and B is defined as a planar direction.

An incontinence pad 11 includes a liquid permeable top sheet 12, a liquid impermeable back sheet 13, and the absorbent body 1 disposed between those. FIG. 9 shows a cross sectional view of the incontinence pad 11. In this figure, although the absorbent body of Embodiment 1 described above is diagrammatically represented as the absorbent body 1, the configuration of the absorbent body is not limited thereto.

The top sheet 12 is disposed so as to face the skin at the crotch portion of the wearer, and allows passage of liquid excrement such as urine. Excrement such as urine that has passed through the top sheet 12 is taken into the absorbent body 1, diffused in a planar direction by the diffusion layer 5, and then moves to the water absorption layer 6 to be absorbed. Therefore, the incontinence pad 11 can immediately absorb the excrement, and the whole water absorbent resin powder included in the water absorption layer 6 can effectively contribute in the absorption of the excrement. The back sheet 13 prevents the excrement from leaking outside.

Side sheets 16 extending in the longitudinal direction A of the incontinence pad 11 are joined on both side edges of the top sheet 12 in the width direction B. The side sheets 16 are formed from a liquid impermeable plastic film, a water-repellent nonwoven fabric, or the like. The side sheets 16 have rise elastic members 17 disposed at inward edges in the width direction of the incontinence pad 11. When the incontinence pad 11 is used, the inward edges of the side sheets 16 rise toward the skin of the wearer through contractive force of the rise elastic members 17 to prevent side-leakage of excrement such as urine.

Hereinafter, the present invention will be described in detail by means of examples. However, the present invention is not limited to the examples below, and changes and embodiments that do not depart from the gist of the present invention are included in the scope of the present invention.

<<Evaluation Methods>>

Water Absorbent Resin Powder (Method for Measuring Absorption Ratio)

Measurement of an absorption ratio is conducted according to JIS K 7223 (1996). A nylon mesh having openings of 63 micrometers (JIS Z8801-1:2000) is cut into a rectangle having a width of 10 cm and a length of 40 cm and folded in half at a center in its longitudinal direction, and both ends thereof are heat-sealed, to produce a nylon bag having a width of 10 cm (inside dimension: 9 cm) and a length of 20 cm. 1.00 g of a measurement sample is precisely weighted and placed into the produced nylon bag such that the sample is uniform at the bottom of the nylon bag. The nylon bag containing the sample is immersed in a saline. After 60 minutes from start of the immersion, the nylon bag is taken out from the saline, and is hung vertically for 1 hour to drain the nylon bag. Then, the mass (F1) of the sample is measured. In addition, the same operation is conducted without using any sample, and a mass F0 (g) at that time is measured. Then, an absorption ratio which is an object is calculated according to the following equation from these masses F1 and F0 and the mass of the sample.

Absorption ratio (g/g)=$(F1-F0)$/mass of sample (Method for Measuring Water Retention Amount)

Measurement of a water retention amount is conducted according to JIS K 7223 (1996). A nylon mesh having openings of 63 micrometers (JIS 28801-1:2000) is cut into a rectangle having a width of 10 cm and a length of 40 cm and folded in half at a center in its longitudinal direction, and both ends thereof are heat-sealed, to produce a nylon bag having a width of 10 cm (inside dimension: 9 cm) and a length of 20 cm. 1.00 g of a measurement sample is precisely weighted and placed into the produced nylon bag such that the sample is uniform at the bottom of the nylon bag. The nylon bag containing the sample is immersed in a saline. After 60 minutes from start of the immersion, the nylon bag is taken out from the saline, and is hung vertically for 1 hour to drain the nylon bag. Then, the nylon bag is dehydrated using a centrifugal hydroextractor (model H-130C special type, manufactured by Kokusan Co., Ltd.). The dehydrating conditions are 143 G (800 rpm) and 2 minutes. A mass (R1) after the dehydration is measured. In addition, the same operation is conducted without using any sample, and a mass R0 (g) at that time is measured. Then, a water retention amount which is an object is calculated according to the following equation from these masses R1 and R0 and the mass of the sample.

$$\text{Water retention amount (g/g)} = (R1 - R0 - \text{mass of sample})/\text{mass of sample}$$

(Method for Measuring Water-Absorption Speed by a Vortex Method)

50 mL of a saline (0.9 wt % sodium chloride solution) and a magnetic stir tip (a diameter at center portion: 8 mm, a diameter at both end portions: 7 mm, length: 30 mm, the surface is coated with a fluororesin) are placed into a 100-mL glass beaker, and the beaker is placed on a magnetic stirrer (HPS-100 manufactured by AS ONE Corporation). The rotational speed of the magnetic stirrer is adjusted to 600 plus or minus 60 rpm, and the saline is stirred. 2.0 g of a sample is added to the solution at the center of the vortex of the saline being stirred, and the water-absorption speed (seconds) of the water-absorbent resin powder is measured according to JIS K 7224 (1996). Specifically, a stopwatch is started at the time when the addition of the water-absorbent resin powder, which is the sample, to the beaker is completed. The stopwatch is stopped at the time when the stirrer tip is covered with the test solution (the time when the vortex disappears and the surface of the solution becomes flat), and the time (seconds) is recorded as a water-absorption speed. The measurement is conducted five times (n=5), the highest and lowest values are removed, and the average of the remaining three values is regarded as a measured value. It is noted that these measurements are conducted at 23 plus or minus 2 degrees centigrade and a relative humidity of 50 plus or minus 5%, and samples are stored in the same environment for 24 hours or longer prior to the measurements and then are subjected to the measurements.

(Moisture Absorption Blocking Ratio)

10.0 g of a sample is uniformly placed into an aluminum cup having a bottom diameter of 52 mm and a height of 22 mm (a foil container, product number: 107, manufactured by Toyo Aluminium Ecko Products Co., Ltd.), and the cup is kept still in a constant temperature and humidity chamber at 40 degrees centigrade and a relative humidity of 80% RH for 3 hours. Then, the sample is lightly sieved with a 12-mesh (opening 1.4 mm) wire mesh, the mass of powdered matter of the measurement sample that has caused blocking due to moisture absorption and has not passed through the 12 mesh and the mass of the sample that has passed through the 12 mesh are measured, and a moisture absorption blocking ratio which is an object is calculated according to the following equation.

$$\text{Moisture absorption blocking ratio (\%)} = (\text{mass of sample not passing through 12 mesh after being kept still})/(\text{mass of sample not passing through 12 mesh after being kept still} + \text{mass of sample passing through 12 mesh after being kept still}) \times 100$$

The measurement is conducted five times (n=5), the highest and lowest values are removed, and the average of the remaining three values is regarded as a measured value. It is noted that these measurements are conducted at 23 plus or minus 2 degrees centigrade and a relative humidity of 50 plus or minus 5%, and samples are stored in the same environment for 24 hours or longer prior to the measurements and then are subjected to the measurements.

(Method for Measuring Liquid-Passing Rate Under Load)

In a 100-mL glass beaker, 0.32 plus or minus 0.005 g of a water-absorbent resin powder that is a sample is immersed in 100 mL of a saline (0.9 wt % sodium chloride solution) and allowed to stand for 60 minutes, thereby swelling the water-absorbent resin powder. Separately, a filtration cylindrical tube is prepared in which a wire mesh (openings: 150 micrometers, a bio-column sintered stainless steel filter 30SUS sold by Sansyo Co., Ltd) and a narrow tube (inner diameter: 4 mm, length: 8 cm) equipped with a cock (inner diameter: 2 mm) are provided at the lower end of an opening portion of a cylinder (inner diameter: 25.4 mm) that stands vertically. All the content within the beaker including the swollen measurement sample is placed into the cylindrical tube in a state where the cock is closed. Next, a cylindrical bar that has a diameter of 2 mm and has, at its end, a wire mesh having openings of 150 micrometers and a diameter of 25 mm is inserted into the filtration cylindrical tube such that the wire mesh comes into contact with the measurement sample, and further a weight is placed such that a load of 2.0 KPa is applied to the measurement sample. In this state, the filtration cylindrical tube is allowed to stand for 1 minute. Then, the cock is opened to allow the solution to flow out, and the time ($T_1$) (seconds) taken until the solution level within the filtration cylindrical tube reaches a 40-mL scale mark from a 60-mL scale mark (i.e., 20 mL of the solution passes) is measured. A liquid-passing rate under a load of 2.0 KPa is calculated from the following equation using the measured time $T_1$ (seconds). It is noted that in the equation, $T_0$ (seconds) is a measured value of a time taken for 20 mL of a saline to pass through the wire mesh in a state where no measurement sample was put in the filtration cylindrical tube.

$$\text{Liquid-passing rate under load (seconds)} = (T_1 - T_0)$$

Diffusibility Improvement Material (Method for Measuring Under-Load Liquid Passing Rate)

FIG. 10 is a schematic diagram for describing a method for measuring an under-load liquid passing rate of the diffusibility improvement material. As shown in (a) of FIG. 10, a diffusibility improvement material 20 which was used as a sample was arranged such that its planar view shape became a square shape whose side was larger than 100 mm. It should be noted that, when a particulate diffusibility improvement material was used, a frame 21 for immobilizing the diffusibility improvement material was provided, and the diffusibility improvement material was arranged within the frame 21. At this moment, the particulate diffusibility improvement material was arranged to become a single layer in the thickness direction and make gaps between particles in a planar direction become as small as possible. When a sheet-like diffusibility improvement material was used, a sheet that was actually used for the absorbent body was cut out such that its planar view shape was a square shape whose side was larger than 100 mm. Then, the diffusibility improvement material within the frame was immersed and kept in saline solution (0.9 mass % sodium chloride solution) for 60 minutes.

As shown in (b) of FIG. 10, a measuring jig 22 includes a stainless steel plate 22a (100 mm×100 mm) having an opening (internal diameter 25.4 mm) at its center, and a cylinder 22b (internal diameter 25.4 mm) attached perpendicularly to the opening portion. The measuring jig 22 was placed on the diffusibility improvement agent 20. A weight 23 was placed on the measuring jig 22 such that a load of 2.0 kPa was applied on a measured sample, and the sample was kept in this state for 1 minute. Then, 150 ml of saline solution was poured in the cylinder, and the time (T) (seconds) from the start of pouring the saline solution until the liquid in the cylinder disappeared was measured, and this time was used as the under-load liquid passing rate. The measurement was conducted by n=5, and value points at the top and bottom were each deleted, and an average of the remaining three points was used as a measured value. It should be noted that the measurements were conducted at 23 plus or minus 2 degrees centigrade and at a relative humidity of 50 plus or minus 5%, and a measurement was conducted after a sample was stored at the same environment for 24 hours or longer.

Manufacturing of Absorbent Body

Absorbent Body 1-1

A spunbond nonwoven fabric was laminated on a polyethylene film. After applying a synthetic-rubber based hot melt adhesive on the spunbond nonwoven fabric, ABS resin particles (particle diameter: 6 mm, under-load liquid passing rate: 10 seconds) were uniformly sprayed on the whole surface thereof as a diffusibility improvement material to form a diffusion layer only having a diffusion region. The planar view shape of the diffusion layer was a rectangular shape in which the length in the longitudinal direction was 30 cm, the length in the width direction was 15 cm, and the thickness was 0.8 cm. After applying a synthetic-rubber based hot melt adhesive on the diffusibility improvement material, a spunbond nonwoven fabric was laminated thereon so as to cover the whole surface.

On the spunbond laminated on the diffusibility improvement material, a spunbond nonwoven fabric was further laminated thereon, and a mixture of pulp and a water absorbent resin powder ("Aqua Pearl (Registered trademark) DS560," manufactured by San-Dia Polymers, Ltd.) was sprayed to form a water absorption layer only having a water absorption region. The planar view shape of the water absorption layer was a rectangular shape in which the length in the longitudinal direction was 30 cm and the length in the width direction was 15 cm. One part of the water absorption layer was cut out in a single streak of a linear slit shape to form an opening region. The linear slit was continuously formed across the whole width of the absorption layer in the longitudinal direction, so as to span over the central line of the absorbent body in the width direction. The length of the slit in the width direction was 3 cm (area ratio with respect to the whole water absorption layer: 20%). With regard to the physical properties of the water absorbent resin powder, the water absorption ratio was 60 g/g, the water retention amount was 42 g/g, the water absorption rate determined by a vortex method was 38 seconds, the moisture absorption blocking rate was 0.1%, and the under-load liquid passing rate was 5 seconds.

After laminating a spunbond nonwoven fabric on the water absorption layer having the opening region and applying a synthetic-rubber based hot melt adhesive thereon, an air-through nonwoven fabric was laminated thereon and the obtained laminated body was pressed to manufacture an absorbent body 1-1. The planar view shape of the absorbent body was a rectangular shape in which the length in the longitudinal direction was 30 cm, the length in the width direction was 15 cm, and the total thickness was 0.8 cm.

The configuration of the obtained absorbent body No. 1 will be described with reference to FIG. 11. FIG. 11 is a schematic sectional view of the absorbent body No. 1. The absorbent body No. 1 includes, sequentially from its lower side (external surface side), a polyethylene film 8, an adhesive layer 9, a spunbond nonwoven fabric 10, an adhesive layer 9, a diffusion layer 5, an adhesive layer 9, a spunbond nonwoven fabric 10, a spunbond nonwoven fabric 10, the water absorption layer 4 including the opening region 3, a spunbond nonwoven fabric 10, an adhesive layer 9, and an air-through nonwoven fabric 18. In the absorbent body No. 1, the spunbond nonwoven fabric 10 exists on the upper side and the lower side of the opening region 3 of the water absorption layer 4.

Absorbent Body 2-1

After applying a synthetic-rubber based hot melt adhesive on a polyethylene film, a mixture of pulp and a water absorbent resin powder was sprayed thereon to form a first water absorption layer only having a water absorption region. The planar view shape of the first water absorption layer was a rectangular shape in which the length in the longitudinal direction was 30 cm and the length in the width direction was 15 cm.

After laminating a spunbond nonwoven fabric on one part of the top surface of the first water absorption layer and applying a synthetic-rubber based hot melt adhesive thereon, ABS resin particles (particle diameter: 6 mm, under-load liquid passing rate: 10 seconds) were uniformly sprayed as a diffusibility improvement material to form a diffusion layer only having a diffusion region. The planar view shape of the diffusion layer was a rectangular shape in which the length in the longitudinal direction was 25 cm, the length in the width direction was 5 cm, and the thickness was 0.8 cm. Furthermore, the diffusion layer was formed such that the central line of the diffusion layer in the width direction and the central line of the first water absorption layer in the width direction match each other. After applying a synthetic-rubber based hot melt adhesive on the diffusibility improvement material, a spunbond nonwoven fabric was laminated thereon so as to cover the whole surface of the diffusibility improvement material.

Next, on the spunbond nonwoven fabric on the diffusion layer for the portion at which the diffusion layer was formed, or on the first water absorption layer for the portion at which the diffusion layer was not formed; a mixture of pulp and a water absorbent resin powder ("Aqua Pearl (Registered trademark) DS560," manufactured by San-Dia Polymers, Ltd.) was sprayed to form a second water absorption layer only having a water absorption region. The planar view shape of the second water absorption layer was a rectangular shape in which the length in the longitudinal direction was 30 cm and the length in the width direction was 15 cm. One part of the second water absorption layer was cut out in a single streak of a linear slit shape to form an opening region. The linear slit was continuously formed across the whole width of the second absorption layer in the longitudinal direction, so as to span over the central line of the absorbent body in the width direction. The length of the slit in the width direction was 3 cm (area ratio with respect to the whole second water absorption layer: 20%).

After applying a synthetic-rubber based hot melt adhesive on the second water absorption layer having the opening region, an air-through nonwoven fabric was laminated thereon and the obtained laminated body was pressed to manufacture an absorbent body 2-1. The absorbent body 2-1 includes each one layer of the second water absorption layer including the opening region, the diffusion layer disposed below the second water absorption layer, and the first water absorption layer disposed below the diffusion layer, wherein the diffusion layer was disposed at least below the opening region. It should be noted that the diffusion layer was formed so as to extend below the water absorption region of the second water absorption layer. The planar view shape of the absorbent body was a rectangular shape in which the length in the longitudinal direction was 30 cm, the length in the width direction was 15 cm, and the total thickness was 0.8 cm. Furthermore, the area ratio of the diffusion layer with respect to the second absorption layer was 27%.

The configuration of the obtained absorbent body 2-1 will be described with reference to FIG. 12. FIG. 12 is a schematic sectional view of the absorbent body 2-1. The absorbent body 2-1 includes, sequentially from its lower side (external surface side), a polyethylene film 8, an adhesive layer 9, the water absorption layer 4, a spunbond nonwoven fabric 10, an adhesive layer 9, a diffusion layer 5, an adhesive layer 9, a spunbond nonwoven fabric 10, the water absorption layer 4 including the opening region 3, an adhesive layer 9, and an air-through nonwoven fabric 18. In the absorbent body 2-1, the spunbond nonwoven fabric 10 exists on the upper side and the lower side of the opening region 3 of the water absorption layer 4.

Absorbent Bodies 2-2, 2-3

Absorbent bodies 2-2 and 2-3 were obtained in a manner similar to the manufacturing of the absorbent body 2-1, except for changing the width and length of the diffusion layer. The diffusion layer of the absorbent body 2-2 had a width of 10.5 cm, a length of 15.0 cm, and an area ratio of 35%. The diffusion layer of the absorbent body 2-3 had a width of 15.0 cm, a length of 15.0 cm, and an area ratio of 50%.

Comparative Absorbent Body 1

After applying a synthetic-rubber based hot melt adhesive on a spunbond nonwoven fabric, a mixture of pulp and a water absorbent resin powder was sprayed thereon to form a water absorption layer only having a water absorption region.

An air-through nonwoven fabric was laminated on the water absorption layer, and the obtained laminated body was pressed to obtain a comparative absorbent body 1 composed of a single water absorption layer.

Comparative Absorbent Body 2

After applying a synthetic-rubber based hot melt adhesive on a spunbond nonwoven fabric, a mixture of pulp and a water absorbent resin powder was sprayed thereon, and one part thereof was cut out in a substantially rectangular shape in planar view (area ratio with respect to the whole water absorption layer: 20%). A water absorption layer was formed by spraying the water absorbent resin powder to the part that was cut out. An air-through nonwoven fabric was laminated on the water absorption layer, and the obtained laminated body was pressed to obtain a comparative absorbent body 2 composed of a single water absorption layer.

Comparative Absorbent Body 3

After applying a synthetic-rubber based hot melt adhesive on a spunbond nonwoven fabric, a mixture of pulp and a water absorbent resin powder was sprayed thereon to form a first water absorption layer only having a water absorption region. After laminating a spunbond nonwoven fabric on the first water absorption layer and applying a synthetic-rubber based hot melt adhesive thereon, the water absorbent resin powder was sprayed thereon to form a second water absorption layer. After laminating a spunbond nonwoven fabric on the second water absorption layer and applying a synthetic-rubber based hot melt adhesive thereon, an air-through nonwoven fabric was laminated thereon and the obtained laminated body was pressed to obtain a comparative absorbent body 3 having two water absorption layers.

The rate of absorbing artificial urine and dryness value were measured for the obtained absorbent bodies 1 and 2 and comparative absorbent bodies Nos. 1 to 3, and the results are shown in Table 1. The measurements were conducted as described below.

<Artificial Urine Absorption Rate, Surface Dryness Value Determined by SDME Method>

An absorbent body was immersed and kept in artificial urine (0.03 wt % potassium chloride, 0.08 wt % magnesium sulfate, 0.8 wt % sodium chloride, and 99.09 wt % deionized water) for 60 minutes for preparation, and a sufficiently wet absorbent body was produced. In addition, an absorbent body was heated and dried at 80 degrees centigrade for 2 hours to produce a sufficiently dried absorbent body. A detector of an SDME (Surface Dryness Measurement Equipment) tester (manufactured by WK system Co., Ltd.) was placed on (at the center in the width direction and center in the length direction) the sufficiently wet absorbent body to configure a 100% dryness value. Next, the detector of the SDME tester was placed on (at the center in the width direction and center in the length direction) the sufficiently dried absorbent body to configure a 0% dryness, and calibration of the SDME tester was conducted. Next, a metal ring (internal diameter 70 mm, length 50 mm) was set at the center of the absorbent body that is to be measured, and 20 ml of artificial urine was poured thereto and the time required until the artificial urine was absorbed was measured to obtain an absorption rate. The metal ring was removed immediately after the absorption had ended, and three SDME detectors were placed at the center of the absorbent body to start measuring the surface dryness value. A value obtained 1 minute after the start of the measurement was used as a surface dryness value. After the absorbent body was kept for 30 minutes, artificial urine was poured thereto for the second time. The operation was conducted similarly to the operation conducted the first time, and the absorption rate of the second time and the surface dryness value of the second time were obtained. The measurements were conducted three times (n=3), and an average of the three measurements was used as a measured value. It should be noted that the artificial urine, the measurement atmosphere, and the keeping atmosphere were 25 plus or minus 5 degrees centigrade and 65 plus or minus 10% RH.

TABLE 1

| | Area ratio of diffusion region (%) | Absorption rate | | | Dryness value | | |
|---|---|---|---|---|---|---|---|
| | | First measurement | Second measurement | Third measurement | First measurement | Second measurement | Third measurement |
| Absorbent body 1-1 | — | 15 seconds | 20 seconds | 20 seconds | 20% | 35% | 40% |
| Absorbent body 2-1 | 27 | 25 seconds | 40 seconds | 60 seconds | 20% | 30% | 35% |
| Absorbent body 2-2 | 35 | 20 seconds | 35 seconds | 45 seconds | 20% | 30% | 35% |
| Absorbent body 2-3 | 50 | 15 seconds | 22 seconds | 31 seconds | 15% | 25% | 35% |
| Comparative absorbent body 1 | — | 35 seconds | 120 seconds | 300 seconds | 22% | 44% | 90% |
| Comparative absorbent body 2 | — | 30 seconds | 180 seconds | 300 seconds | 20% | 72% | 90% |
| Comparative absorbent body 3 | — | 34 seconds | 195 seconds | 300 seconds | 22% | 64% | 90% |

As can be understood from Table 1, the absorbent bodies 1-1, and 2-1 to 2-3, each having an opening region on a water absorption layer and a diffusion region below the opening region, have a fast absorption rate and excellent dryness. This is thought to be caused by an improvement in diffusibility of the artificial urine in the absorbent body due to the sprayed diffusibility improvement material.

On the other hand, the comparative absorbent bodies 1 to 3 are cases where there are no layers having a diffusion region formed thereon, and those have a slow absorption rate and are inferior in terms of dryness. Since the comparative absorbent bodies 1 to 3 do not have a layer with a diffusion region formed thereon, gel-blocking occurs easily when the water absorbent resin powder absorbs water, and permeability to the absorbent body and dryness are unlikely to improve. This is thought to be the reason why the absorption rate in the first measurement, the absorption rate in the second measurement, and the dryness in the second measurement and beyond were inferior.

The present invention includes the following embodiments.

Embodiment 1

An absorbent body having at least two or more layers, the absorbent body comprising:

a water absorption layer having a water absorption region where a water absorbent resin powder is disposed and a thickness-direction-penetrating opening region; and a layer having a diffusion region where a diffusibility improvement material having an under-load liquid passing rate of 15 seconds or less is disposed, as a lower layer of the water absorption layer, wherein the lower layer has the diffusion region disposed at least a part of a portion located below the opening region.

Embodiment 2

The absorbent body according to embodiment 1, wherein the diffusion region of the lower layer has a planar view shape of a circular shape, an elliptical shape, a polygonal shape, a polygonal shape having rounded corners, or a slit shape.

Embodiment 3

The absorbent body according to embodiment 1 or 2, wherein the lower layer is a diffusion layer only having the diffusion region.

Embodiment 4

The absorbent body according to any one of embodiments 1 to 3, wherein the opening region is formed in a slit shape.

Embodiment 5

The absorbent body according to any one of embodiments 1 to 4, wherein the water absorption layer includes a water absorbent resin powder satisfying the following requirements:

Absorption ratio: 50 g/g or more; and
Water retention amount: 25 g/g or more.

Embodiment 6

An absorbent article comprising the absorbent body according to any one of embodiments 1 to 5.

INDUSTRIAL APPLICABILITY

The absorbent body of the present invention can be suitably used as, for example, an absorbent article used for absorbing body fluid discharged from the human body, and can be used particularly suitably as absorbent articles such as incontinence pads, disposable diapers, sanitary napkins and breast-milk pads.

REFERENCE SIGNS LIST

1: absorbent body, 2: water absorption region, 3: opening region, 4: water absorption layer, 5: diffusion layer, 6: diffusion region, 7: water diffusion-and-absorption layer, 8: polyethylene film, 9: adhesive layer, 10: spunbond nonwoven fabric, 11: incontinence pad (absorbent article), 12: top sheet, 13: back sheet, 16: side sheet, 17: rise elastic member, 18: air-through nonwoven fabric

The invention claimed is:

1. An absorbent body having at least two or more layers, the absorbent body comprising:
   a water absorption layer having a water absorption region where a water absorbent resin powder is disposed and a thickness-direction-penetrating opening region; and
   a layer having a diffusion region where a granular diffusibility improvement material composed of at least one kind of resin particles selected from the group consisting of polypropylene particles, polystyrene particles and acrylonitrile-butadiene-styrene copolymer resin particles, and having a particle diameter in a range from 0.05 mm to 10 mm and an under-load liquid passing rate of 15 seconds or less, is disposed, as a lower layer of the water absorption layer,
   wherein the lower layer has the diffusion region disposed at least a part of a portion located below the opening region, and the resin particles are present in particulate form in the absorbent body.

2. An absorbent article comprising the absorbent body according to claim 1.

3. The absorbent body according to claim 1, wherein the diffusion region of the lower layer has a planar view shape of a circular shape, an elliptical shape, a polygonal shape, a polygonal shape having rounded corners, or a slit shape.

4. An absorbent article comprising the absorbent body according to claim 3.

5. The absorbent body according to claim 1, wherein the lower layer is a diffusion layer only having the diffusion region.

6. An absorbent article comprising the absorbent body according to claim 5.

7. The absorbent body according to claim 1, wherein the opening region is formed in a slit shape.

8. An absorbent article comprising the absorbent body according to claim 7.

9. The absorbent body according to claim 1, wherein the water absorption layer includes a water absorbent resin powder satisfying the following requirements:
   Absorption ratio: 50 g/g or more and 70 g/g or less; and
   Water retention amount: 25 g/g or more and 60 g/g or less,
      wherein the water absorbent resin powder is a cross-linked polymer mainly composed of acrylic acid having carboxy groups thereof that are at least partially neutralized.

10. An absorbent article comprising the absorbent body according to claim 9.

* * * * *